United States Patent
Kim et al.

(10) Patent No.: US 9,554,762 B2
(45) Date of Patent: Jan. 31, 2017

(54) METHOD AND APPARATUS FOR OBTAINING X-RAY IMAGE OF REGION OF INTEREST OF OBJECT

(71) Applicant: SAMSUNG ELECTRONICS CO., LTD., Suwon-si (KR)

(72) Inventors: Tae-kyun Kim, Seoul (KR); Sung-nam Kim, Seoul (KR); Jae-chool Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/301,820

(22) Filed: Jun. 11, 2014

(65) Prior Publication Data

US 2015/0110245 A1 Apr. 23, 2015

(30) Foreign Application Priority Data

Jun. 11, 2013 (KR) .................. 10-2013-0066794
May 21, 2014 (KR) .................. 10-2014-0061170

(51) Int. Cl.
*A61B 6/00* (2006.01)
*A61B 6/06* (2006.01)
*A61B 5/00* (2006.01)
*A61B 6/03* (2006.01)
*A61B 6/04* (2006.01)
*A61B 5/055* (2006.01)

(52) U.S. Cl.
CPC .............. *A61B 6/48* (2013.01); *A61B 5/0037* (2013.01); *A61B 6/469* (2013.01); *A61B 6/488* (2013.01); *A61B 6/5241* (2013.01); *A61B 5/055* (2013.01); *A61B 6/03* (2013.01); *A61B 6/0457* (2013.01); *A61B 6/06* (2013.01); *A61B 6/465* (2013.01); *A61B 6/545* (2013.01)

(58) Field of Classification Search
CPC ....... G06T 3/20; G06T 3/4038; A61B 5/0037; A61B 6/06; A61B 6/488; A61B 6/5241; A61B 6/545
USPC ......................................................... 382/132
See application file for complete search history.

(56) References Cited

U.S. PATENT DOCUMENTS 7,114,849 B2 10/2006 Atzinger et al.
7,555,100 B2 * 6/2009 Wang et al. ............... 378/98.12
(Continued)

FOREIGN PATENT DOCUMENTS

JP 2001-245140 A 9/2001
JP 2007-260027 A 10/2007
(Continued)

OTHER PUBLICATIONS

Communication, Issued by the International Searching Authority, Dated Sep. 1, 2014, in counterpart International Application No. PCT/KR2014/005111.

(Continued)

*Primary Examiner* — David J Makiya
*Assistant Examiner* — Dani Fox
(74) *Attorney, Agent, or Firm* — Sughrue Mion, PLLC

(57) ABSTRACT

A method of obtaining an X-ray image, the method including: obtaining a first image of an object; receiving a determination whether the first image includes an entirety of a region of interest (ROI); and obtaining a second image of the object, the second image including a portion of the ROI which is absent in the first image.

19 Claims, 33 Drawing Sheets

(56) References Cited

U.S. PATENT DOCUMENTS

| | | | |
|---|---|---|---|
| 2006/0104545 A1 | 5/2006 | Matsumoto | |
| 2006/0198499 A1 | 9/2006 | Spies et al. | |
| 2006/0241370 A1 | 10/2006 | Kramp et al. | |
| 2007/0071172 A1 | 3/2007 | Mollus et al. | |
| 2008/0037714 A1 | 2/2008 | Sakaida et al. | |
| 2010/0091949 A1 | 4/2010 | Sato | |
| 2010/0138044 A1 | 6/2010 | Maack et al. | |
| 2010/0260494 A1* | 10/2010 | Sutton | G02B 3/0037 396/268 |
| 2011/0188726 A1* | 8/2011 | Nathaniel et al. | 382/132 |
| 2012/0050327 A1 | 3/2012 | Takekoshi | |
| 2012/0257709 A1 | 10/2012 | Oota et al. | |
| 2013/0184537 A1* | 7/2013 | Konuma | A61B 5/0033 600/300 |

FOREIGN PATENT DOCUMENTS

| | | |
|---|---|---|
| JP | 2010-94209 A | 4/2010 |
| JP | 2011-4856 A | 1/2011 |
| JP | 2012-50515 A | 3/2012 |
| JP | 2012-50605 A | 3/2012 |
| KR | 10-2009-0078506 A | 7/2009 |

OTHER PUBLICATIONS

Communication, Issued by the European Patent Office, Dated Oct. 23, 2014, in counterpart European Application No. 14171968.2.

\* cited by examiner

METHOD AND APPARATUS FOR OBTAINING X-RAY IMAGE OF REGION OF INTEREST OF OBJECT

CROSS-REFERENCE TO RELATED APPLICATIONS

This application claims priority from Korean Patent Application No. 10-2013-0066794, filed on Jun. 11, 2013, and Korean Patent Application No. 10-2014-0061170, filed on May 21, 2014, in the Korean Intellectual Property Office, the disclosures of which are incorporated herein in their entireties by reference.

BACKGROUND

1. Field

Apparatuses and methods consistent with exemplary embodiments relate to obtaining an image including a region of interest (ROI) of an object, and more particularly, to obtaining a medical image including an ROI of an object, such as an X-ray image, by combining a first image of the object and a second image including a portion of the ROI of the object.

2. Description of the Related Art

Medical apparatuses that use X-rays are used for radiographic medical imaging.

The X-ray process is performed at least once to obtain an X-ray image including organs of interest of an object, i.e., a patient. Thus, if the X-ray process is repeatedly conducted on the entire object a plurality of times, a radiation amount to which the object is exposed increases, and an increase in the radiation exposure may cause side effects resulting in health problems.

Thus, apparatuses and methods are needed for obtaining an image of an ROI of an object by using an X-ray that radiates a small number of times and over a small area.

SUMMARY

Exemplary embodiments may address at least the above problems and/or disadvantages and other disadvantages not described above. However, exemplary embodiment are not required to overcome the disadvantages described above, and may not overcome any of the problems described above.

One or more exemplary embodiments include a method of obtaining an image of an ROI of an object under a condition of limited exposure to the object.

One or more exemplary embodiments include an apparatus for obtaining a medical image of an ROI of an object, such as an X-ray image.

According to an aspect of an exemplary embodiment, there is provided a method of obtaining an X-ray image of an ROI of an object, the method including: obtaining a first image of the object; determining whether the first image includes the ROI; selecting an imaging mode to re-image the object based on the determining; and obtaining a second image of the object according to the selected imaging mode.

The second image may include a portion or the entirety of the ROI. For example, the first image may be analyzed in order to reduce a degree of exposure of the object to radiation, and an imaging mode may be selected, in which a second image including a portion lacking in the first image is imaged. The above operations may be performed on an object existing at a predetermined position, and the first image of the object existing at the predetermined position may be a reference for selecting an imaging mode.

The imaging mode may be selected from a plurality of imaging modes corresponding to imaging areas having different sizes. The plurality of imaging modes may include an entire ROI imaging mode and a partial imaging mode.

The determining whether the first image includes the ROI may include comparing a reference image of the object and the first image.

The reference image may be selected from previously stored images based on properties of the object.

The method may further include extracting at least one feature point related to the ROI from the first image. The determining whether the first image includes the ROI may include comparing the at least one feature point extracted from the first image with a feature point related to the ROI included in the reference image.

The number and a position of the at least one feature point may be differently defined in advance according to a size and a position of the ROI.

The comparing of the at least one feature point extracted from the first image with the feature point related to the ROI included in the reference image may include comparing the number and a position of the feature point related to the ROI included in the reference image and the number and a position of the at least one feature point extracted from the first image.

The method may further include extracting a boundary line of the ROI from the first image. The determining whether the first image includes the ROI may include comparing the boundary line extracted from the first image and a boundary line of the ROI included in the reference image.

The comparing of the boundary line extracted from the first image and the boundary line of the ROI included in the reference image may include determining a similarity between the boundary line extracted from the first image and the boundary line of the ROI included in the reference image.

The imaging mode may include an entire ROI imaging mode in which the entire ROI of the object is re-imaged and a partial imaging mode in which a portion of the ROI of the object is re-imaged.

The method may further include determining a portion of the ROI to be additionally imaged, when the partial imaging mode is selected. The second image including the determined portion may be obtained.

The determining of the portion to be additionally imaged may include: estimating a portion of the ROI that is not included in the first image; and determining an additional imaging area including the estimated portion by using size information of the first image.

The estimating of the portion of the ROI not included in the first image may include determining a size and a position of the portion not included in the first image based on the size and the position of the ROI included in the reference image.

The size information of the first image may include at least one of height information and width information of the first image.

The determining of the additional imaging area may include determining an imaging area such that all portions of the ROI corresponding to the determined size and position of the portion not included in the first image are included in the additional imaging area based on at least one of the height information and the width information of the first image.

The method may further include receiving an additional imaging area of the object, as an external input signal, when the partial imaging mode is selected. The second image corresponding to the received additional imaging area may be obtained.

The method may further include setting an imaging condition based on the selected imaging mode. The obtaining of the second image may include obtaining an X-ray image of the object according to the set imaging condition.

The imaging condition may include at least one of a position of an X-ray source, an amount of collimation, a position of an X-ray detector, and an image resolution.

The method may further include combining the first image and the second image.

The second image may include at least one template to be used in combining the second image with the first image. The combining of the first image and the second image may include stitching the second image with the first image by using the at least one template.

The at least one template may be differently set based on at least one of properties of the object, a size of the ROI, and a position of the ROI.

The second image may include a plurality of templates to be used in combining the second image with the first image, wherein the combining of the first image and the second image includes: applying different weights to the plurality of templates; and stitching the first image to the second image based on the applied weights.

According to an aspect of an exemplary embodiment, there is provided an apparatus for obtaining an X-ray image of an ROI of an object, the apparatus including: an image obtainer for obtaining a first image of the object; an area determiner for determining whether the first image includes the ROI; and an imaging mode selector for selecting an imaging mode to re-image the object based on the determining, wherein a second image of the object is obtained by using the image obtainer according to the selected imaging mode, and the second image includes the entirety or a portion of the ROI. For example, the first image may be analyzed in order to reduce a degree of exposure of the object to radiation, and an imaging mode may be selected, in which a second image including a portion lacking in the first image is imaged. The above operations may be performed on an object existing at a predetermined position, and the first image of the object existing at the predetermined position may be a reference for selecting an imaging mode.

The imaging mode may be selected from a plurality of imaging modes corresponding to imaging areas having different sizes. The plurality of imaging modes may include an entire ROI imaging mode and a partial imaging mode.

The area determiner may compare a reference image of the object and the first image.

The reference image may be selected based on properties of the object from previously stored images.

The apparatus may further include a feature point extractor for extracting at least one feature point related to the ROI from the first image, wherein the area determiner further includes a comparator that compares the at least one feature point extracted from the first image with a feature point of the ROI included in the reference image.

The number and a position of the at least one feature point may be defined differently in advance according to a size and a position of the ROI.

The comparator may compare the number and a position of a feature point of the ROI included in the reference image and the number and a position of the at least one feature point extracted from the first image.

The apparatus may further include a boundary line extractor for extracting a boundary line of the ROI from the first image, wherein the area determiner further includes a comparator that compares the boundary line extracted from the first image with a boundary line of the ROI included in the reference image.

The comparator may determine a similarity between the boundary line extracted from the first image and a boundary line of the ROI included in the reference image.

The imaging mode may include an entire ROI imaging mode in which the entire ROI of the object is re-imaged and a partial imaging mode in which a portion of the ROI of the object is re-imaged.

The apparatus may further include an additional imaging determiner that determines a portion of an ROI that is to be additionally imaged, as a partial imaging mode is selected.

The additional imaging determiner may include an insufficient portion estimator that estimates a portion of an ROI not included in the first image and an additional imaging area determiner that determines an additional imaging area including the portion estimated by using the insufficient portion estimator by using size information of the first image.

The insufficient portion estimator may determine a size and a position of a portion not included in the first image based on a size and a position of an ROI included in a reference image.

The size information of the first image may include at least one of height information and width information of the first image.

The additional imaging area determiner may determine an imaging area such that all of portions of an ROI corresponding to the determined size and the position of the portion are included in the additional imaging area, based on at least one of the height information and the width information of the first image.

The apparatus may further include an external input receiver that receives an additional imaging area of an object, as an external input signal, as a partial imaging mode is selected, and a second image corresponding to the received additional imaging area may be obtained.

The apparatus may further include an imaging condition setter that sets an imaging condition based on the selected imaging mode, and a second image may be obtained as an X-ray image of an object according to a set imaging condition.

An imaging condition may include at least one of a position of an X-ray source, an amount of collimation, a position of an X-ray detector, and an image resolution.

The apparatus may further include an image combiner that combines an obtained first image and an obtained second image.

The second image may include at least one template to be used in combining the second image with the first image, and the image combiner may stitch the first image and the second image by using at least one template.

The at least one template may be set differently based on at least one of properties of an object, a size of an ROI, and a position of an ROI.

The second image may include a plurality of templates to be used in combining the second image with the first image, and the image combiner may further include a weight applier that applies different weights to a plurality of templates. The image combiner may stitch an obtained first image and an obtained second image based on the applied weights.

According to an aspect of an exemplary embodiment, there is provided a method of obtaining an X-ray image, the method including: obtaining a first image of an object; receiving a determination whether the first image includes an entirety of a region of interest (ROI); and obtaining a second image of the object, the second image including a portion of the ROI which is absent in the first image.

The receiving the determination may include: comparing a reference image of the object and the first image.

The method may include selecting the reference image from previously stored images based on properties of the object.

The method may include extracting one or more first feature points of the ROI from the first image, wherein the receiving the determination may include comparing the one or more first feature points with one or more second feature points of a corresponding ROI of the reference image.

A number and positions of the one or more first feature points are defined in advance, based on different criteria including at least one of a size of the ROI and a position of the ROI within the object.

The comparing the one or more first feature points with the one or more second feature points may include: comparing a number and positions of the one or more second feature points and a number and positions of the one or more first feature points, wherein the first image is determined to include the ROI when the number of the one or more second feature points coincide with that of the one or more first feature points and the positions of the one or more second feature points substantially coincide with that of the one or more first feature points.

The method may include extracting a first boundary line of the ROI from the first image, wherein the receiving the determination may include comparing the first boundary line and a second boundary line of a corresponding ROI of the reference image.

The method wherein the comparing the first boundary line and the second boundary line may include determining a similarity between the first boundary line and the second boundary line, wherein the first image is determined to include the ROI when the first boundary line is substantially similar to the second boundary line.

The obtaining the second image may include providing a first imaging mode and a second imaging mode to be selected to re-image the object based on the received determination, the first imaging mode is a mode in which an entire ROI of the object is re-imaged, and the second imaging mode is a mode in which the portion of the ROI of the object is re-imaged.

The method may include receiving a determination of the portion of the ROI to be re-imaged; selecting the second imaging mode; and obtaining the second image including the determined portion of the ROI, in the second imaging mode.

The receiving the determination of the portion of the ROI to be re-imaged may include: estimating the portion of the ROI that is not included in the first image; and receiving a determination of an additional imaging area to include the estimated portion by using size information of the first image.

The estimating the portion of the ROI may include determining a size and a position of the portion not included in the first image based on the size and the position of the ROI included in the reference image.

The size information of the first image may include at least one of a height and a width of the first image.

The receiving the determination of the additional imaging area may include determining an imaging area such that all portions of the ROI corresponding to the determined size and position of the portion not included in the first image are included in the additional imaging area based on at least one of the height and the width of the first image.

The method may include receiving a selection of an additional imaging area of the object; selecting the second imaging mode; and obtaining the second image corresponding to the received additional imaging area, in the second imaging mode.

The method may include selecting the first imaging mode or the second imaging mode based on the received determination; setting an imaging condition based on the selected first imaging mode or the second imaging mode, wherein the obtaining the second image may include obtaining an X-ray image of the object according to the set imaging condition.

The imaging condition may include at least one of a position of an X-ray source, an amount of collimation, a position of an X-ray detector, and an image resolution.

The method may include combining the first image and the second image.

The method may include providing a template for the second image, wherein the combining the first image and the second image may include stitching the second image with the first image by using the template.

The template is set based on different criteria including at least one of properties of the object, a size of the ROI, and a position of the ROI.

The method may include providing a plurality of templates for the second image, wherein the combining the first image and the second image may include: applying different weights to different templates of the plurality of templates; and stitching the first image to the second image based on the weights applied to the templates.

According to an aspect of an exemplary embodiment, there is provided an apparatus for obtaining an X-ray image of a region of interest (ROI) of an object, the apparatus including: an image obtainer configured to obtain a first image of an object; and an area determiner configured to determine whether the first image includes an entirety of a region of interest (ROI) of the object, wherein a second image of the object is obtained by the image obtainer according to determining by the area determiner, and the second image includes a portion of the ROI which is determined to be absent in the first image.

The area determiner compares a reference image of the object and the first image, to determine whether the first image includes the ROI.

The reference image is selected based on properties of the object from previously stored images.

The apparatus may include a feature point extractor configured to extract one or more first feature points related to the ROI from the first image, wherein the area determiner further may include a comparator configured to compare the one or more first feature points with one or more second feature points of a corresponding ROI of the reference image.

A number and positions of the one or more first feature points are defined in advance based on different criteria including at least one of a size of the ROI and a position of the ROI within the object.

The comparator compares a number and positions of the one or more second feature points and a number and positions of the one or more first feature points, and the area determiner determines that the first image includes the ROI when the number of the one or more second feature points coincides with that of the one or more first feature points and the positions of the one or more second feature points substantially coincide with that of the one or more first feature points.

The apparatus may include a boundary line extractor configured to extract a first boundary line of the ROI from the first image, wherein the area determiner further may include a comparator that compares the first boundary line with a second boundary line of a corresponding ROI of the reference image.

The comparator determines a similarity between the first boundary line and a second boundary line, and the area determiner determines that the first image includes the ROI when the first boundary line is substantially similar to the second boundary line.

According to an aspect of an exemplary embodiment, there is provided an imaging method including: obtaining a main image in a main imaging operation set to image a region of interest (ROI) of an object; receiving a determination that the main image lacks a portion of the ROI intended to be included into the main image; and obtaining an additional image of the object which includes the portion of the ROI absent in the main image, in an auxiliary imaging operation.

The obtaining the main image in the main imaging operation may include: receiving a determination of the ROI to be imaged; dividing the ROI into imaging areas of a predetermined size; obtaining separate X-ray images of the imaging areas, by moving at least one of an X-ray detector and an X-ray source by a first distance corresponding to the predetermined size, a respective number of times; and combining the separate X-ray images into the main image.

The obtaining the additional image of the object in the auxiliary imaging operation may include: receiving a determination of a smallest additional area to be re-imaged in the auxiliary imaging operation; and moving the X-ray detector or the X-ray source a second distance once, the second distance having a smaller value than the first distance and corresponding to a size of the additional area to be re-imaged.

The receiving the determination of the smallest additional area may include receiving an external input of a user via an input device, by which the user indicates the smallest additional area to be imaged.

The input device may include a screen which displays the main image, and a user interface is configured to receive an input of the user to indicate the smallest additional area.

The user interface may include at least one of: a window configured to receive a selection of a size of the smallest additional area; a pullout menu configured to display a list of dimensions of the smallest additional area and receive a selection of the dimensions of the smallest additional area; a sliding bar tool slidably superimposed on the main image and configured to receive a selection of the smallest additional area; and an adjustable window tool adjustably superimposed on the main image and configured to receive a selection of the smallest additional area.

The receiving the determination of the smallest additional area may include: comparing the main image with a reference image; and estimating the portion of the ROI that is absent from the main image.

The receiving may include determining a size of the portion of the ROI absent in the main image and the method further may include: providing, in the auxiliary imaging operation, a selection of a first imaging mode in which an entire ROI of the object is re-imaged and a second imaging mode in which the portion of the ROI of the object is re-imaged; selecting, in the auxiliary imaging operation, the first imaging mode to re-image the entire ROI, based on the determining that the size of the portion of the ROI absent in the main image is substantially equal to a size of the entire ROI; and selecting, in the auxiliary imaging operation, the second imaging mode to image only the portion of the ROI, based on the determining that the size of the portion of the ROI absent in the main image is smaller than the size of the ROI.

According to an aspect of an exemplary embodiment, there is provided an imaging method including: obtaining a first image of an object; receiving a determination of whether the first image includes an entirety of a region of interest (ROI) intended to be imaged; providing a first imaging mode in which an entire ROI is re-imaged and a second imaging mode in which only a portion of the ROI absent from the first image is imaged again; selecting the first imaging mode or the second imaging mode based on the determination; and obtaining a second image of the object according to the selected first imaging mode or the selected second imaging mode.

According to an aspect of an exemplary embodiment, there is provided an imaging method including: providing a first image of an object on a screen; receiving a determination of whether the first image includes an entirety of a region of interest (ROI) intended to be imaged; receiving a selection of an additional area to be imaged again, based on the determination, the additional area including a portion of the ROI absent from the first image; obtaining a second image of the object according to the selection of the additional area; and combining the first image and the second image into an image including the entirety of the ROI.

According to an aspect of an exemplary embodiment, there is provided a medical imaging method including: capturing a first image of an object; receiving a determination of a location of a portion of a region of interest (ROI) intended to be included into but absent from the first image; capturing a second image of the object only to include the portion of the ROI absent in the first image; and combining the first image and the second image.

The receiving the determination may include identifying a location of a first edge corresponding to an edge of the first image proximate the ROI intended to be included into the first image, and determining a location of a second edge, based on the location of the first edge, and the capturing may include capturing the second image only to include the portion of the ROI from the first edge to the second edge.

According to an aspect of an exemplary embodiment, there is provided an imaging method including: capturing a first X-ray image of an object to include a region of interest (ROI); displaying the first X-ray image on a screen; receiving a determination that the first X-ray image lacks a portion of the ROI intended to be included into the first X-ray image; providing a location of a first edge corresponding to an edge of the captured first X-ray image proximate the ROI intended to be included into the first image; capturing a second X-ray image of the object to include the portion of the ROI absent in the first X-ray image, by using the location of the first edge; and combining the first X-ray image with the second X-ray image.

The providing may include determining a second edge based on the location of the first edge, and the capturing the second X-ray image may include capturing the second X-ray image only to include the portion of the ROI from the first edge to the second edge.

The capturing the second X-ray image may include: adjusting a range of X-ray radiation by adjusting one of a size and a position of a collimator of an X-ray source, to include only the portion of the ROI from the first edge to the second edge.

According to an aspect of an exemplary embodiment, there is provided a method of obtaining an image of a region of interest (ROI) of an object, the method including: obtaining a first image of the object; obtaining a second image of the object; and generating an image including the ROI of the object by using the first image and the second image, wherein the second image has a different size from the first image and includes a portion or an entirety of the ROI.

The second image is smaller than the first image.

According to an aspect of an exemplary embodiment, there is provided a method of obtaining an image of a region of interest (ROI), the method including: determining sizes of a first image and a second image that are to be imaged based on a size of the ROI; obtaining the first image of the object based on the determined size; obtaining the second image of the object based on the determined size; and generating an image including the ROI of the object by using the first image and the second image, wherein the second image has a different size from the first image and includes a portion or an entirety of the ROI.

The generating the image may include generating the image by combining the first image and the second image by overlapping the first image and the second image by a predetermined size.

According to an aspect of an exemplary embodiment, there is provided an apparatus for obtaining an image of a region of interest (ROI) of an object, the apparatus including: an image obtainer configured to obtain a first image and a second image of the object; and an image generator configured to generate an image including the ROI of the object by using the first image and the second image, wherein the second image has a different size from the first image and includes a portion or an entirety of the ROI.

The second image is smaller than the first image.

According to an aspect of an exemplary embodiment, there is provided an apparatus for obtaining an image of a region of interest (ROI) of an object, the apparatus including: an image size determiner configured to determine sizes of a first image and a second image to be imaged based on a size of the ROI; an image obtainer configured to obtain the first image and the second image of the object based on the determined sizes; and an image generator configured to generate an image including the ROI of the object by using the first image and the second image, wherein the second image has a different size from the first image and includes a portion or an entirety of the ROI.

The image generator is configured to generate the image by combining the first image and the second image by overlapping the first image and the second image by a predetermined size.

The predetermined size by which the first image and the second image are overlapped is in a range from about 35 mm to about 90 mm.

According to an aspect of an exemplary embodiment, there is provided a computer-readable recording medium having embodied thereon a program for executing the method described above.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
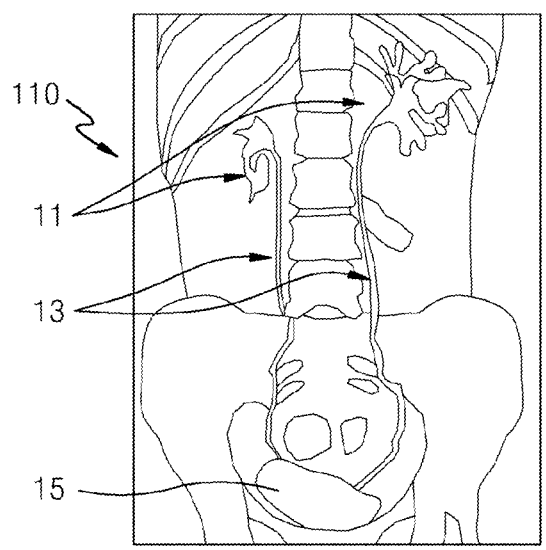
FIG. 1 illustrates an exemplary image including a kidney, a ureter, and a bladder of an object.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

It will be understood that the terms "comprises" and/or "comprising" or "includes" and/or "including" when used in this specification, specify the presence of stated elements, but do not preclude the presence or addition of one or more other elements. Terms such as " . . . unit" and "module" stated in the specification denote units that process at least one function or operation, and they may be implemented by using hardware, software, or a combination of hardware and software.

In the specification, an image may refer to multi-dimensional data representing discrete image elements (e.g., pixels of a two-dimensional (2D) image and voxels of a three-dimensional (3D) image). For example, an image may include a medical image of an object, which is obtained using X-rays, computed tomography (CT), magnetic resonance imaging (MRI), ultrasound, or other medical imaging systems.

Also, an object may refer to a human being or an animal or a part of a human being or an animal. For example, the object may include a liver, heart, uterus, brain, breast, abdomen, or blood vessels. In addition, the object may include a phantom. A phantom may refer to a material that has a highly approximate volume to a density of an organism and an effective atom number and may include a spherical phantom that has similar properties to those of a human body.

A user may be a medical expert, such as a doctor, a nurse, a medical technologist, or a medical image expert, but the present invention is not limited thereto.

Expressions such as "at least one of," when preceding a list of elements, modify the entire list of elements and do not modify the individual elements of the list.

According to the method and apparatus for obtaining an X-ray image including an ROI of an object, an additional imaging area of an object which may be obtained when an image of organs that are located in different parts of the object are captured may be appropriately selected to thereby minimize an amount of radiation exposure with respect to the object. In addition, an unnecessary increase in imaging time due to repeated re-imaging may be prevented.

FIG. 1 illustrates an exemplary image including a kidney, a ureter, and a bladder of an object.

According to the related art, when an organ of interest is not included in an X-ray image of an object, at least one of an X-ray source unit and an X-ray detecting unit is moved to re-image the entire object so that all organs of interest are included in an X-ray image.

For example, when an X-ray image 110 of an object is obtained, and the entirety or a portion of a tissue that is of interest (e.g., a kidney 11, a ureter 13, and a bladder 15) is not included in the obtained X-ray image, an image of an area including the tissue of interest has to be re-acquired. In this case, a position of the object or an imaging device may be adjusted such that the tissue of the organ of interest (e.g., the kidney 11, the ureter 13, or the bladder 15) is completely included in an X-ray image, thereby obtaining the X-ray image of the object again.

For example, to obtain an X-ray image including all of the kidney 11, the ureter 13, and the bladder 15 of an object, re-imaging may be conducted at least twice according to skills of the user regarding an X-ray imaging apparatus. In other words, as internal structures may vary according to objects, even a skilled user may have to repeat X-ray imaging of an object to obtain an X-ray image that contains all areas of the interest. For example, positions of organs may be different according to the gender, age, or body type of an object, and thus, it is difficult to always capture an image that contains every area of interest (e.g., tissues such as the kidney 11, the ureter 13, and the bladder 15).

The more times an X-ray image of an object is recaptured, the greater is a cumulative amount of X-ray irradiated to the object.

In addition, when a position of an object or an X-ray imaging apparatus has to be adjusted so that all areas of interest are included in an X-ray image, the time taken for X-ray imaging also increases.

Accordingly, if not all areas of interest are included in the obtained X-ray image, X-ray imaging of a smallest area including portions (e.g., insufficient portions) that were missing contained in the previously obtained X-ray image may be performed instead of X-ray re-imaging of the entire the object, and the captured plurality of images may be combined, thereby reducing unnecessary exposure of the object to radiation and reducing an imaging time.

Figure 2A:
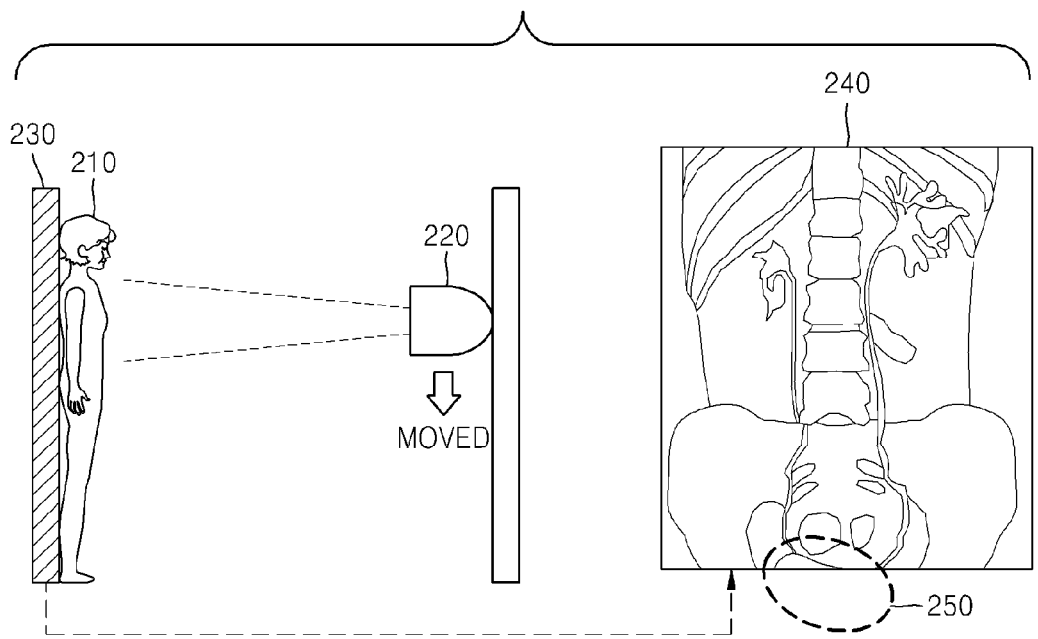
FIGS. 2A, 2B, and 2C are schematic views illustrating a method of obtaining an X-ray image including an ROI of an object, according to an exemplary embodiment.
Figure 2B:
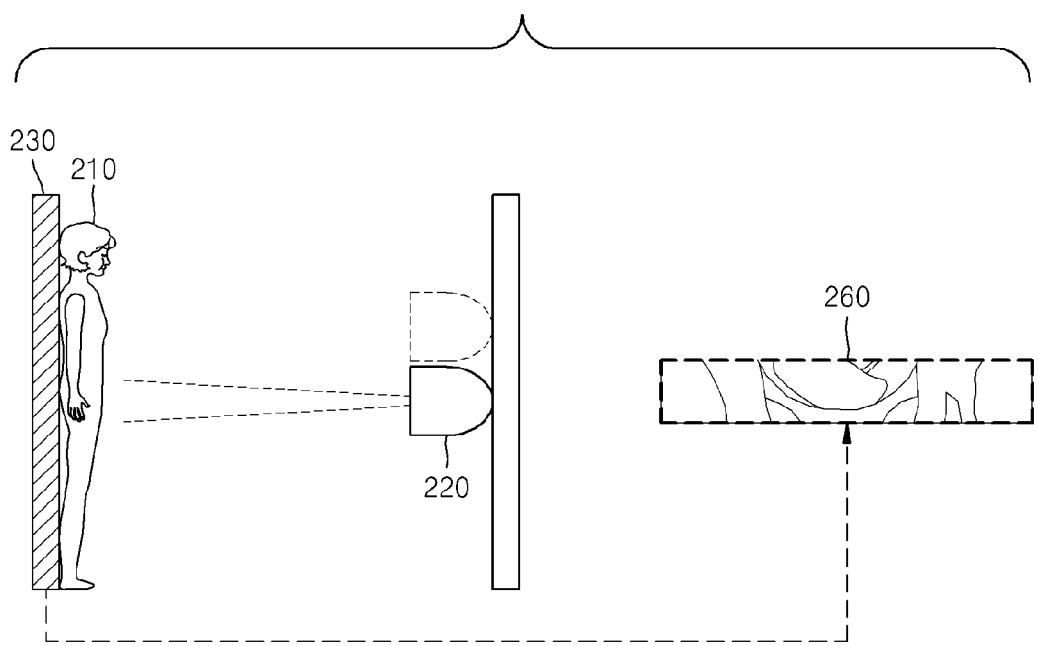
Figure 2C:
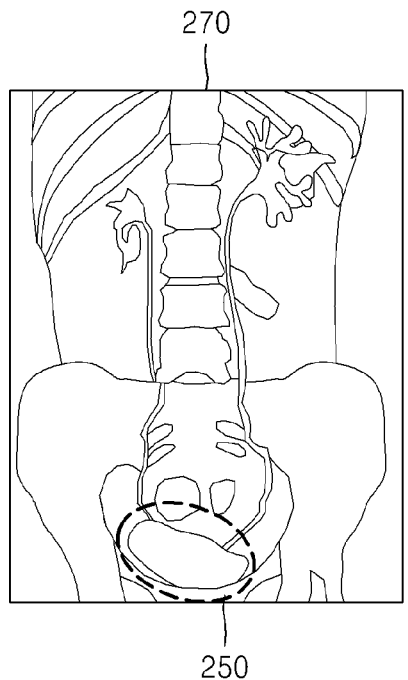

FIGS. 2A through 2C are schematic views illustrating a method of obtaining an X-ray image including an ROI of an object according to an exemplary embodiment.

As illustrated in FIG. 2A, an X-ray image 240 of an object 210 located between an X-ray source 220 and an X-ray detector 230 may be obtained. For example, a user may have intended to obtain an X-ray image that includes all of the kidney 11, the ureter 13, and the bladder 15 of the object 210 but the X-ray image 240 obtained does not include a bladder 250 (schematically shown as missing by a broken line).

In order to obtain an image 260 of the bladder which is not included by previous imaging, as illustrated in FIG. 2B, imaging may be conducted after adjusting a position of the X-ray source 220 or a position of the object 210. A size and a position of a collimator that adjusts a range of X-ray radiation may be adjusted.

As illustrated in FIG. 2C, by combining a plurality of X-ray images, (e.g., the X-ray images 240 and 260), an X-ray image 270 including all of the ROIs may be obtained.

According to an exemplary embodiment, in order to obtain an image of the bladder 250, the image 260 may be obtained by irradiating an X-ray to a minimal extent such that the bladder 250 is included in the image 260, and organs such as the kidney 11 or the ureter 13 which is disposed above the bladder 250 and is already imaged does not have to be exposed to radiation again.

Figure 3A:
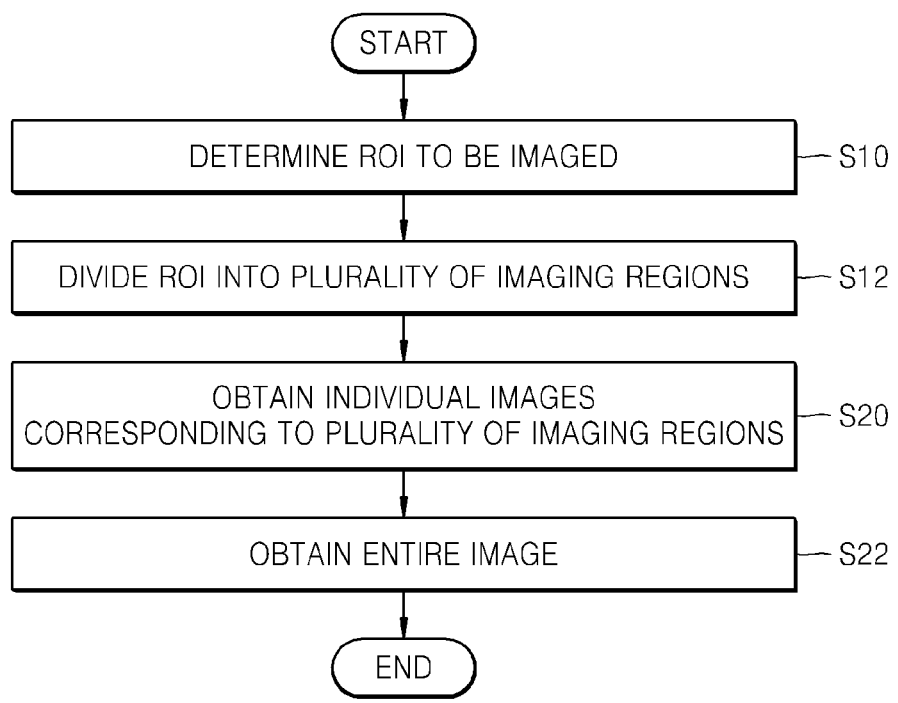
FIGS. 3A and 3B are flowcharts illustrating a method of obtaining an X-ray image including an ROI of an object, according to an exemplary embodiment.
Figure 3B:
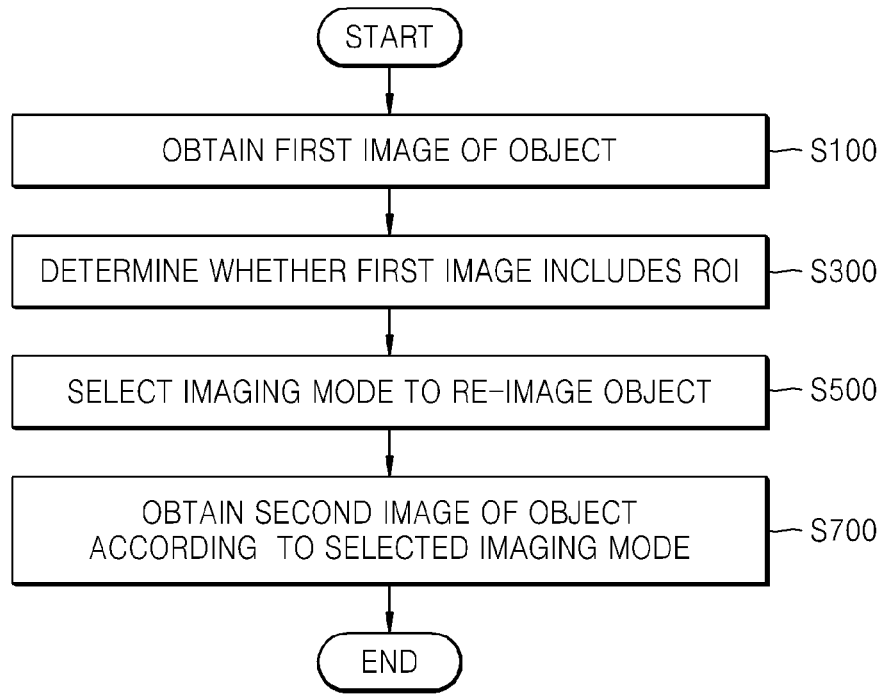

FIGS. 3A and 3B are flowcharts illustrating a method of obtaining an X-ray image including an ROI of an object, according to an exemplary embodiment. FIG. 3A is a flowchart of a main imaging operation. FIG. 3B is a flowchart of a correction imaging operation or a supplemental imaging operation that is performed in connection with the main imaging operation in regard to FIG. 2.

In operation S10, an ROI to be imaged may be determined. The determined ROI may be divided into a plurality of imaging regions in operation S12.

FIG. 3I illustrates an X-ray tube 20 and a detector 30 that are used to obtain an image of an object by sensing an X-ray 22 having passed through an object 10.

A size of an X-ray tube or a detector of a medical equipment including an X-ray imaging equipment or a resolution of an image obtained by using the equipment may be limited so that an image including a long ROI with respect to an object is not obtained through one-time imaging, i.e., an image including a long ROI may be obtained as a combination image obtained by combining smaller image portions that are imaged with respect to the object. An image of a smaller portion to obtain a combination image with respect to the object may be obtained by rotating at least one of the X-ray tube 20 and the detector 30 or by, for example, vertically moving the X-ray tube 20 or the detector 30 in a perpendicular direction 24. A combination image with respect to the object 10 may be obtained by combining images of portions of the object described above by using various image combination methods. For example, an ROI 131 of an object may be divided into imaging regions 132, 134, and 136 of the same or different lengths in a preset direction that is parallel to the perpendicular direction 24. An individual image of each imaging region may be obtained.

Figure 32:
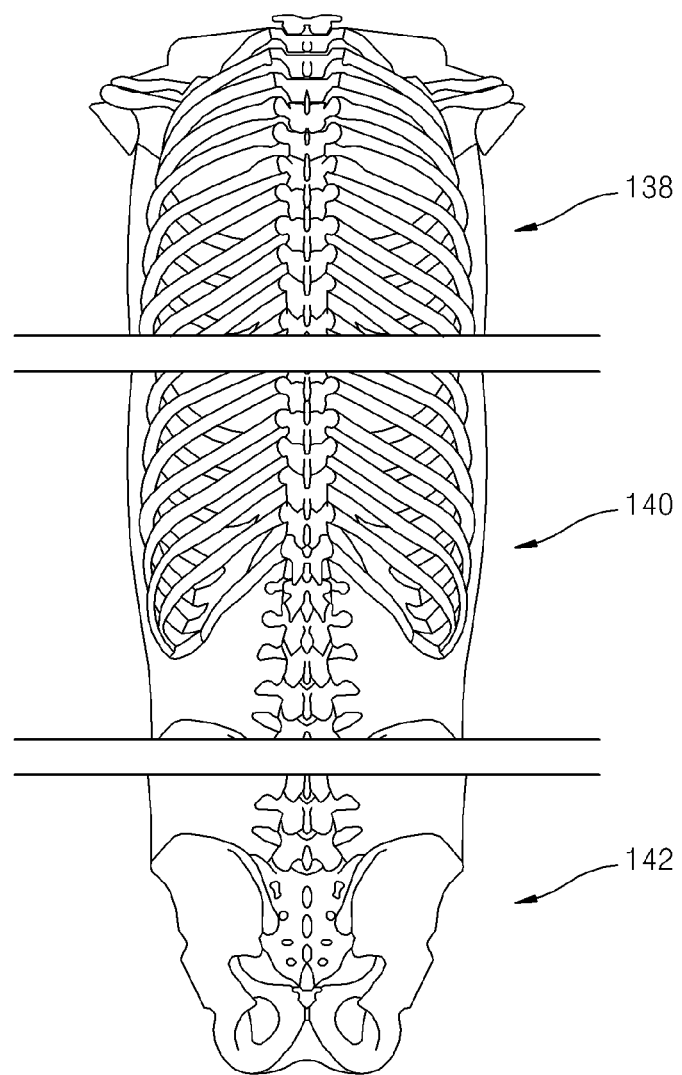
FIG. 32 shows individual images respectively corresponding to imaging areas of an object, according to an exemplary embodiment.

FIG. 32 shows individual images respectively corresponding to imaging areas of an object, according to an exemplary embodiment.

Referring to FIGS. 3A and 32, for example, individual images 138, 140, and 142 respectively corresponding to the imaging regions 132, 134, and 136 may be obtained in operation S20. The individual images 138, 140, and 142, for example, may be combined to an entire X-ray image in which an ROI of an object is included.

Operations S10, S12, S20 or S22 described above may be performed by using an apparatus 2000 described below with reference to FIG. 20. For example, operations S10, S12, S20 or S22 may be performed by using the imaging obtainer 2100 of the apparatus 2000. Also, operations S10, S12, S20 or S22 may be performed by a different processor of the apparatus 2000 or by a separate apparatus. In some instances, operations S12 and S20 may be omitted.

As illustrated in FIG. 3B, the method of obtaining an X-ray image including an ROI of an object, according to an exemplary embodiment, may include: obtaining a first image of an object (operation S100); determining whether the first image includes an ROI (operation S300); selecting an imaging mode to re-image the object based on a result of the determining (operation S500); and obtaining a second image of the object according to the selected imaging mode (operation S700). The first image obtained may correspond to an X-ray image in which an ROI of an object is included.

The second image according to an exemplary embodiment may include the entirety or a portion of the ROI. For example, the first image may be analyzed in order to reduce a degree of exposure of the object to radiation, and an imaging mode may be selected, in which a second image including a portion lacking in the first image is imaged. The above operations may be performed on an object existing at a predetermined position, and the first image of the object existing at the predetermined position may be a reference for selecting an imaging mode.

Also, an imaging mode may be selected from a plurality of imaging modes corresponding to imaging areas having different sizes. The plurality of imaging modes may include an entire ROI imaging mode, e.g., a first imaging mode, and a partial imaging mode, e.g., a second imaging mode.

Figure 4:
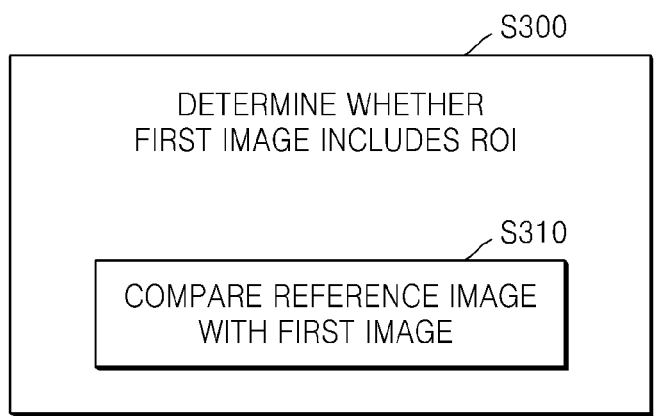
FIG. 4 illustrates an operation of determining whether a first image includes an ROI, according to an exemplary embodiment.

FIG. 4 illustrates an operation of determining whether the first image includes an ROI, according to an exemplary embodiment.

The determining whether the first image includes an ROI (operation S300) may include comparing a reference image of the target image and the first image (operation S310). The comparing images according to an exemplary embodiment may include a series or operations that are conducted to determine a similarity between a plurality of images, which will be described later.

FIGS. 5A through 5E illustrate reference images according to an exemplary embodiment.

Figure 5C:
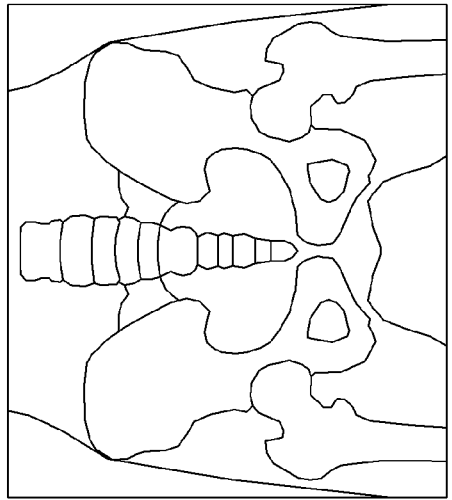
FIGS. 5A, 5B, 5C, 5D, and 5E illustrate reference images according to an exemplary embodiment.
Figure 5B:
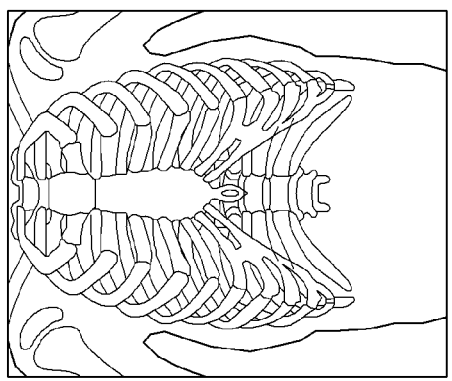
Figure 5A:
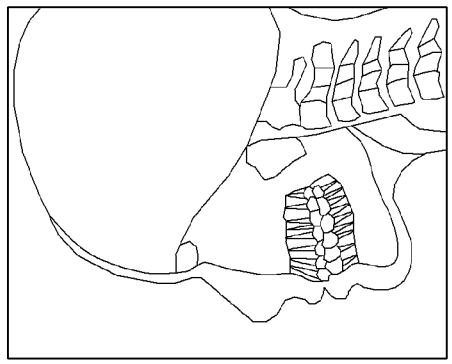
Figure 5E:
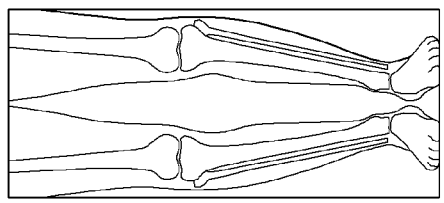
Figure 5D:
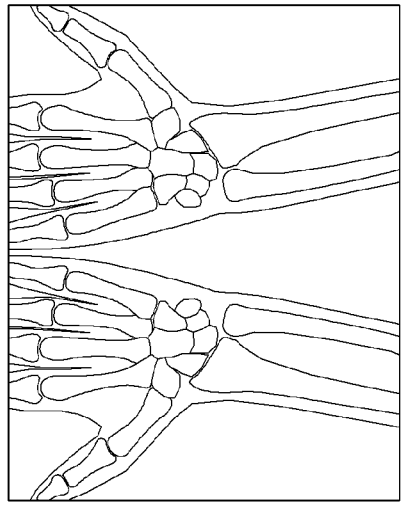

FIG. 5A illustrates an example of a reference image of a skull and a cervical vertebrae of an object. FIG. 5B is an example of a reference image of a chest of the object. FIG. 5C is an example of a reference image of a lower abdominal portion of the object. FIG. 5D is an example of a reference image of arms of the object. FIG. 5E is an example of a reference image of legs of the object.

The reference images of the object may be statistically determined for respective portions (for example, body parts) of the object and stored in a database in advance. For example, predetermined elements (e.g., the number of ribs or positions of diaphragms included in the images) found in X-ray images of a chest of a plurality of objects are extracted, and the most frequently extracted elements are defined as common features based on a frequency that the elements appear in X-ray images of the chest of the plurality of target object, and the X-ray images of the chest of the objects including the common features may be defined as the reference images and stored.

The reference images according to an exemplary embodiment may be selected based on properties of an object that is to be imaged, from images of the plurality of objects stored in advance. The properties of the object according to an exemplary embodiment may include the age, gender, height, weight, body type, part to be imaged, medical history of the object to be imaged and so on.

In other words, a reference image may be selected based on at least one of the age, gender, height, weight, body type, part to be imaged, and medical history of the object to be imaged, from images of a plurality of objects that are stored in advance. For example, from the images of a plurality of objects that are stored in advance, a reference image of a chest of a child and that of a chest of an adult may be differently selected. Also, as illustrated in FIGS. 5A through 5E, reference images may be differently selected according to a portion of an object to be imaged.

Figure 6:
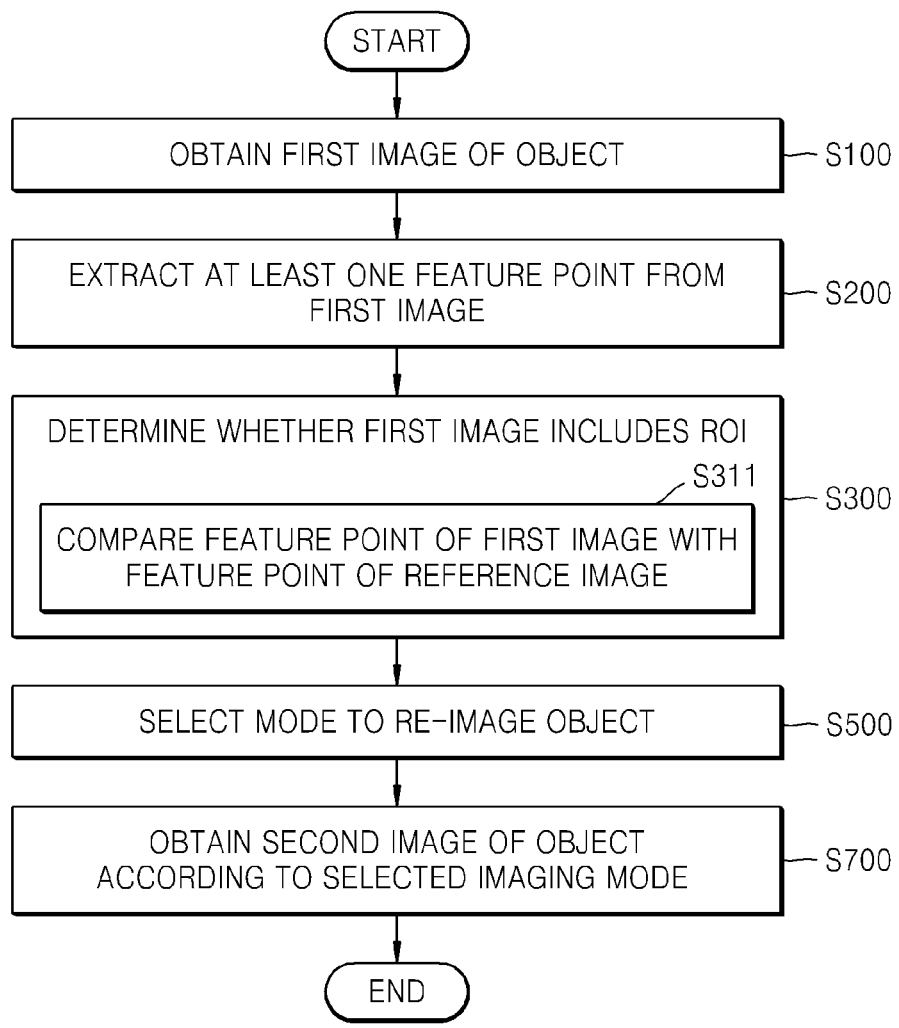
FIG. 6 is a flowchart illustrating a method of determining whether a first image includes an ROI, according to an exemplary embodiment.

FIG. 6 is a flowchart illustrating a method of determining whether a first image includes an ROI, according to an exemplary embodiment.

The method of determining whether a first image includes an ROI according to an exemplary embodiment may further include extracting at least one feature point related to an ROI from the first image (operation S200). Determining whether the first image includes an ROI (operation S300) may include comparing a feature point extracted from the first image with a feature point regarding an ROI included in a reference image (operation S311).

For example, whether the first image includes an ROI may be determined by using a scale-invariant feature transform (SIFT) method using a feature point of an object or a model-based matching method.

FIGS. 7A through 7E illustrate feature points according to an exemplary embodiment.

The number and a position of at least one feature point according to an exemplary embodiment may be defined in advance according to a size and a position of an ROI.

The feature point according to an exemplary embodiment may include a predetermined point to distinguish, for example, tissues included in an X-ray image of an object. For example, the feature point may be used as an identifier to identify at least one of a shape, size, and position of a tissue or the like included in an X-ray image of an object.

Figure 7C:
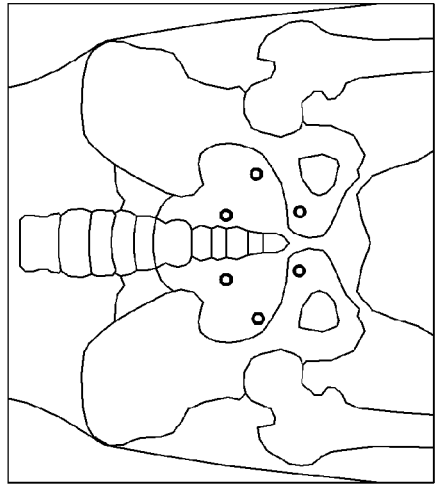
FIGS. 7A, 7B, 7C, 7D, and 7E illustrate feature points according to an exemplary embodiment.
Figure 7B:
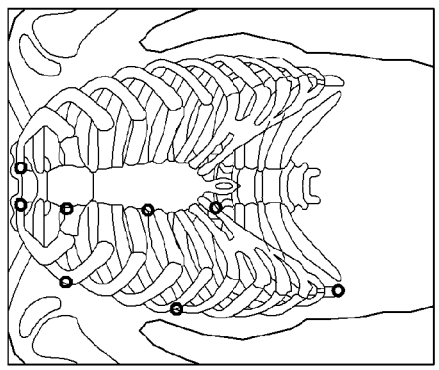
Figure 7E:
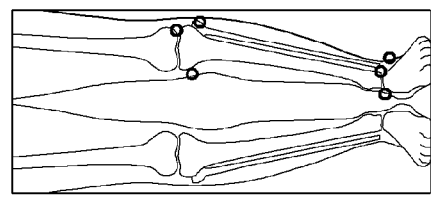
Figure 7A:
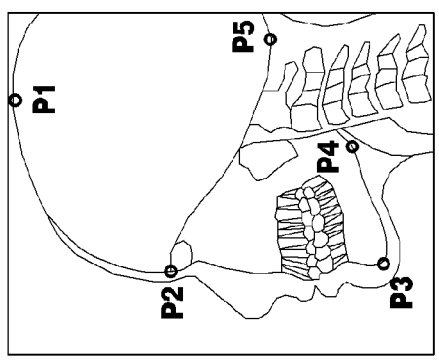
Figure 7D:
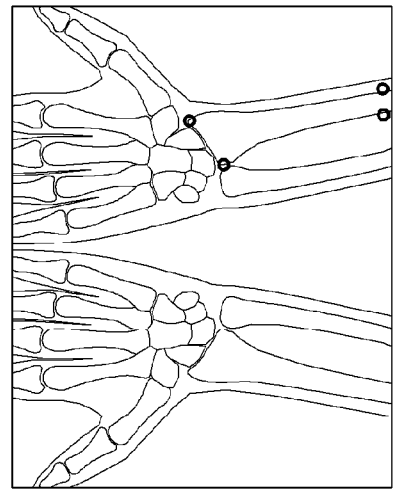

As illustrated in FIG. 7A, for example, a plurality of feature points (e.g., feature points P1 through P5) may indicate that an image includes a skull of an object. That is, the skull of the object may be identified in an X-ray image based on a plurality of feature points (e.g., the feature points P1 through P5).

As illustrated in FIGS. 7B, 7C, 7D, and 7E, at least one feature point of each portion of an object may be determined in advance.

An operation of comparing a feature point extracted from a first image and a feature point of an ROI included in a reference image, according to an exemplary embodiment, may include comparing the number and a position of a feature point of the ROI included in the reference image and the number and a position of a feature point extracted from the first image.

For example, when a skull of an object is an ROI, and only some feature points, for example, feature points P1', P2', and P5' corresponding to the feature points P1, P2, and P5 of the reference image, are found in the first image, then it may be determined that the feature points P3' and P4' corresponding to the feature points P3 and P4 of the reference image do not exist in the first image. Thus, it may be determined that the first image does not include an entire ROI. That is, a lower jaw corresponding to the feature points P3 and P4 of the reference image may be determined as not being included in the first image.

Figure 8:
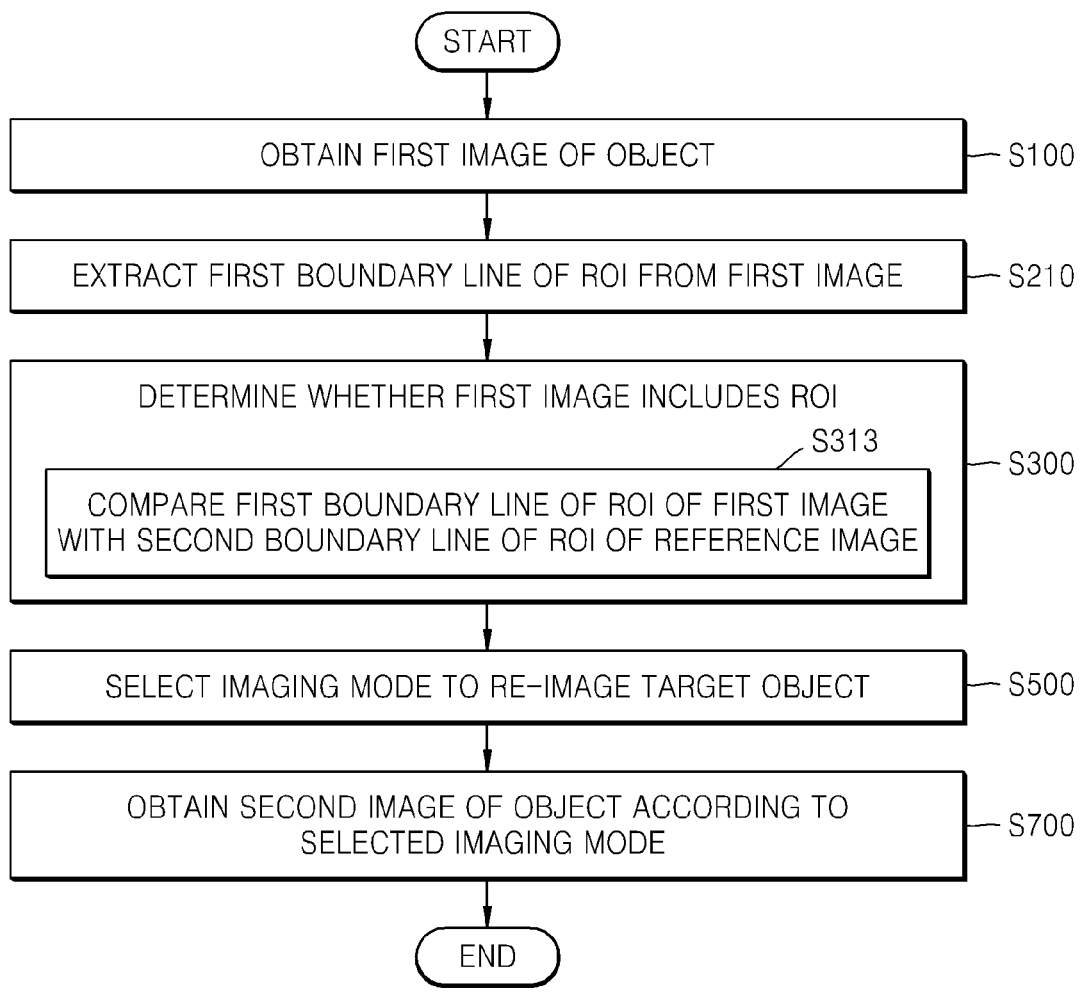
FIG. 8 is a flowchart illustrating a method of determining whether a first image includes an ROI, according to an exemplary embodiment.

FIG. 8 is a flowchart illustrating a method of determining whether a first image includes an ROI, according to an exemplary embodiment.

The method of determining whether a first image includes an ROI, according to an exemplary embodiment, may further include extracting a boundary line (i.e., a first boundary line) of the ROI from the first image (operation S210).

Determining whether the first image includes the ROI (operation S300) may include comparing a boundary line extracted from the first image and a boundary line (i.e., a second boundary line) of the ROI included in a reference image (operation S313).

FIGS. 9A through 9E illustrate boundary lines according to an exemplary embodiment.

Similarly to the feature points, the boundary line according to an exemplary embodiment may include a predetermined line used to distinguish, for example, a tissue included in an X-ray image of an object. The line may be a solid line, a dotted line, or an alternating long and short dashed line, but is not limited thereto. The boundary line may be used as an identifier to identify at least one of a shape, size, and position of the tissue included in the X-ray image of the object.

Figure 9A:
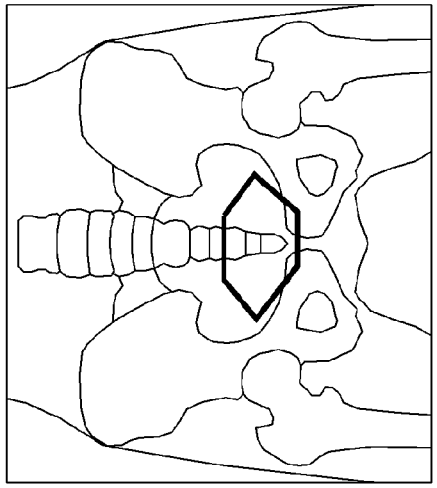
FIGS. 9A, 9B, 9C, 9D, and 9E illustrate boundary lines according to an exemplary embodiment.
Figure 9B:
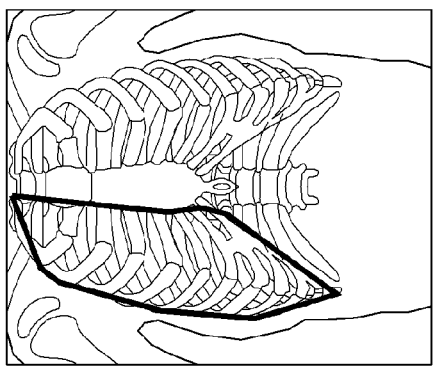
Figure 9C:
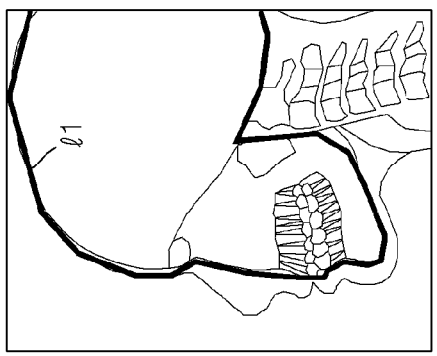
Figure 9D:
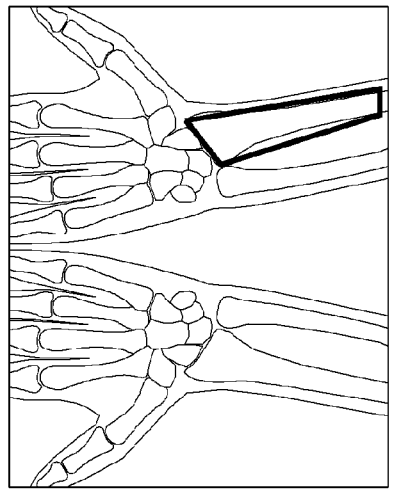
Figure 9E:
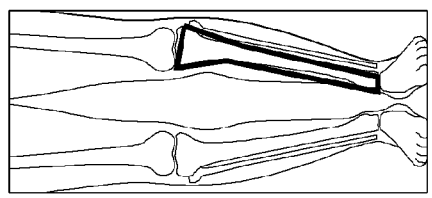

As illustrated in FIG. 9A, for example, a skull of an object may be identified by a boundary line 11. As illustrated in FIGS. 9B, 9C, 9D, and 9E, a boundary line of each portion of the object may be edited and may be determined in advance.

Comparing a boundary line extracted from a first image and a boundary line of an ROI included in a reference image, according to an exemplary embodiment, may include determining a similarity between the boundary line extracted from the first image and the boundary line of the ROI included in the reference image.

For example, by determining a similarity between two boundary lines 11 and 11' based on whether a boundary line (e.g., 11') extracted from the first image is cut or deformed compared to a boundary line (e.g., 11) of the ROI included in the reference image, it may be determined whether the first image includes the ROI.

For example, when a similarity between the boundary line 11 of the ROI included in the reference image and the boundary line 11' extracted from the first image is about 95% or greater, it may be determined that the ROI is included in the first image, and when the similarity is less than about 75%, it may be determined that the ROI is not included in the first image. However, a value of the similarity used as a reference for the above determination is not limited thereto.

Figure 10A:
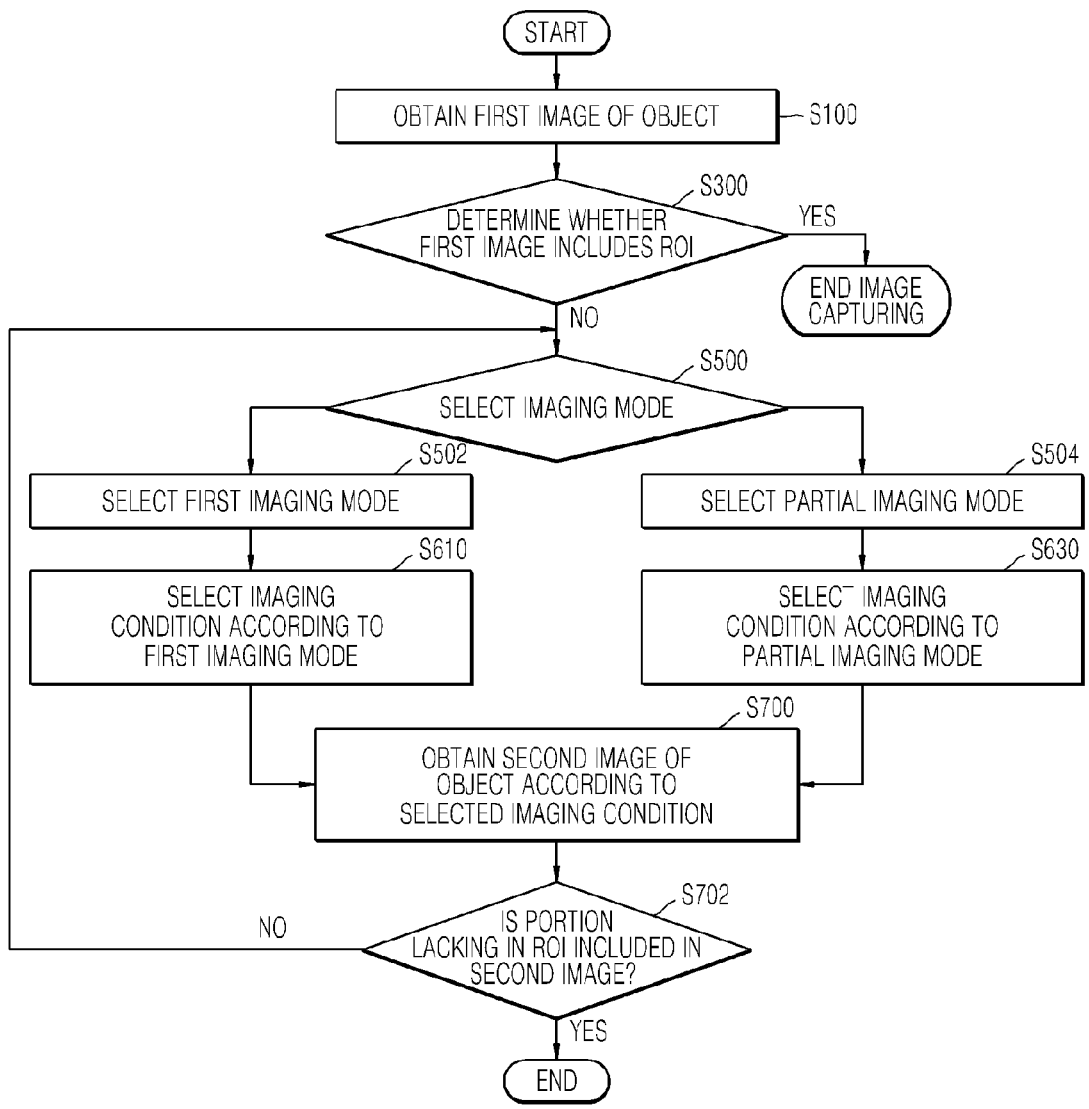
FIGS. 10A and 10B illustrate a method of selecting an imaging mode according to an exemplary embodiment.
Figure 10B:
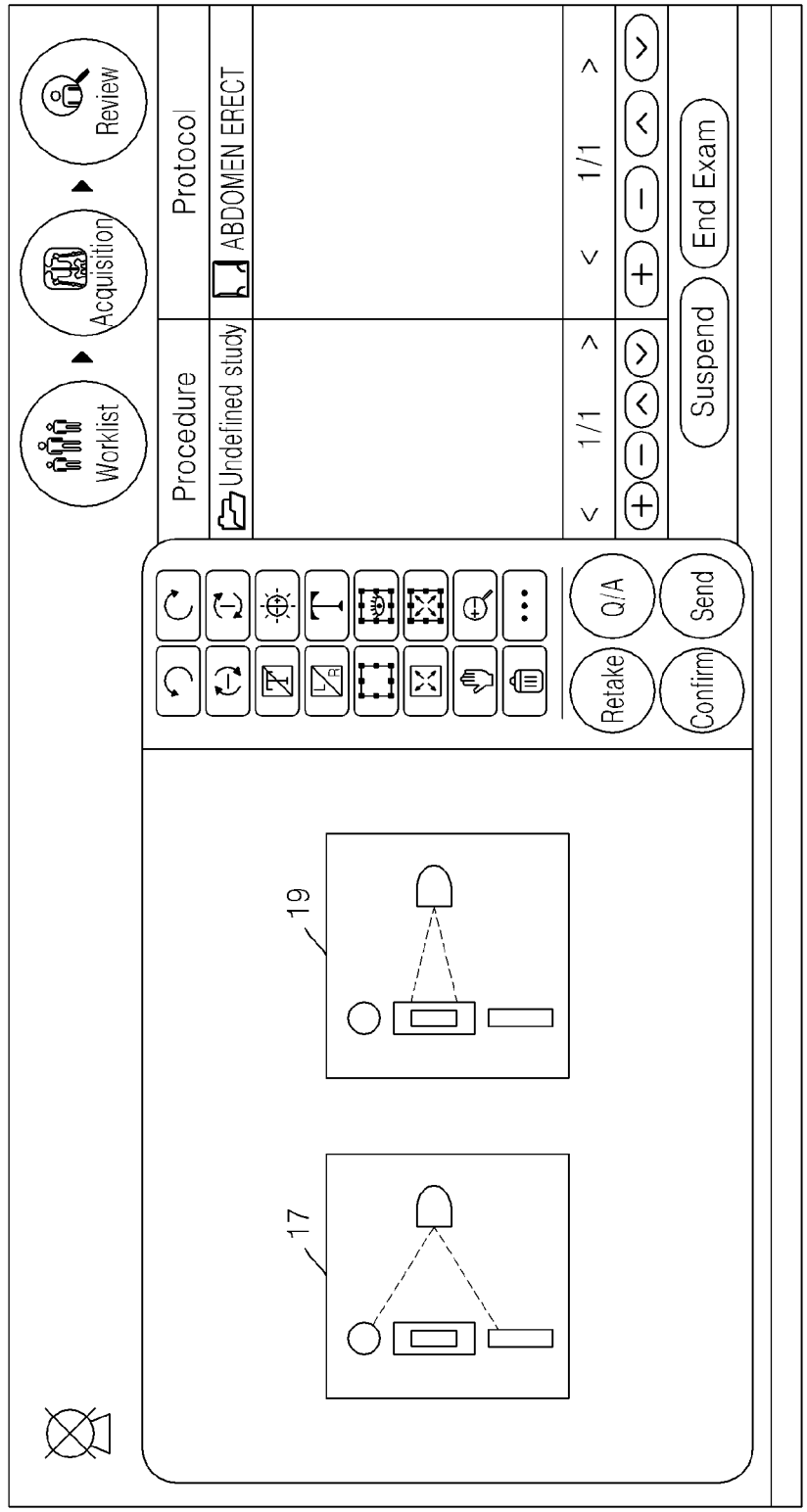

FIGS. 10A and 10B illustrate a method of selecting an imaging mode according to an exemplary embodiment.

An imaging mode according to an exemplary embodiment may include an entire ROI imaging mode in which the entire ROI of an object is imaged again and a partial imaging mode in which a portion of an ROI of an object is imaged again.

According to an exemplary embodiment, as illustrated in FIG. 10A, a first image of an object may be obtained (operation S100), and whether the first image includes an ROI may be determined (operation S300), and when the first image includes an ROI, imaging may end.

When it is determined that the first image does not include an ROI in operation S300, an imaging mode to re-image the object may be selected (operation S500). An imaging mode may be automatically selected by using an X-ray imaging apparatus or may be manually selected via an external input signal input by a user.

For example, when the entire ROI imaging mode is selected, an imaging condition according to the entire ROI imaging mode may be selected (operation S610). For example, the imaging condition may include at least one of an X-ray radiation intensity, a position of an X-ray source, an amount of collimation (e.g., a range of radiation determined by at least one of a position and a size of a collimator), a position of an X-ray detector, and an image resolution.

In operation S700, a second image of the object may be obtained according to the selected imaging condition in operation S610 described above.

In operation S702, it may be determined whether a portion which was lacking is included in the second image. If the portion lacking in the ROI is included in the second image, the method may end. However, if the portion lacking in the ROI is not included in the second image, the method may return to operation S500 to reselect an imaging mode. Operation S702 may be omitted.

As another example, in operation S504, the partial imaging mode may be selected, and an imaging condition according to the partial imaging mode may be selected (operation S630). As described above, the imaging condition may include at least one of an X-ray radiation intensity, a position of an X-ray source, an amount of collimation (e.g., a range of radiation determined by at least one of a position and a size of a collimator), a position of an X-ray detector, and an image resolution.

In operation S700, a second image of the object may be obtained according to the imaging condition selected in operation S630.

FIG. 10B illustrates an imaging mode that is set based on an external input signal or the like by a user, according to an exemplary embodiment.

A user interface may be provided, via which an imaging mode is selected according to an exemplary embodiment.

An entire ROI imaging mode and a partial imaging mode according to an exemplary embodiment may be provided in the form of a graphic user interface (GUI) including, for example, an image as illustrated in FIG. 10B. For example, the entire ROI imaging mode GUI may be displayed as an image 17 of FIG. 10B. The partial imaging mode GUI may be displayed as an image 19 of FIG. 10B. In operation S500, an imaging mode corresponding to an image selected by movement of a cursor or a user's touch (for example, the image 17 or the image 19) may be selected. The entire ROI imaging mode may be provided as a text such as "ENTIRE ROI IMAGING" instead of the image 17 of FIG. 10B, and the partial imaging mode may also be provided as a text such as "PARTIAL IMAGING" instead of the image 19 of FIG. 10B.

Figure 11:
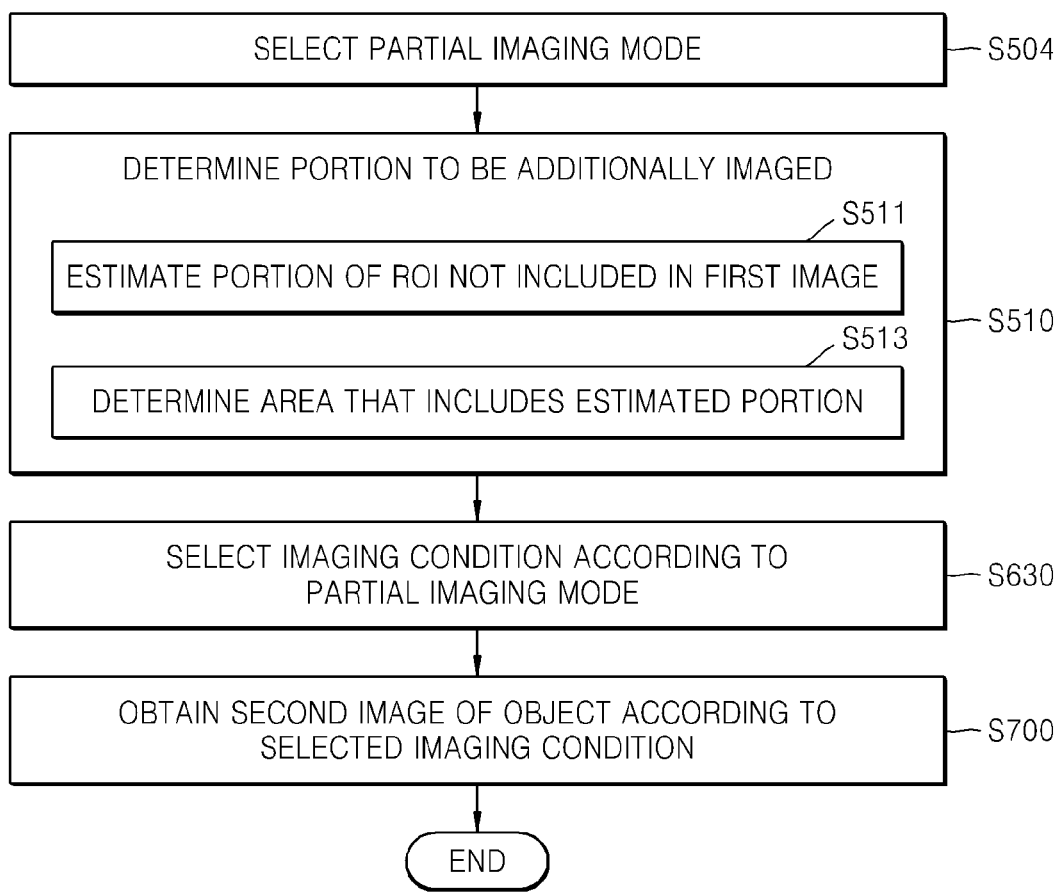
FIG. 11 is a flowchart illustrating a method of determining an additional imaging area when a partial imaging mode is selected, according to an exemplary embodiment.

FIG. 11 is a flowchart illustrating a method of determining an additional imaging area when a partial imaging mode is selected, according to an exemplary embodiment.

The method according to an exemplary embodiment may further include determining a portion to be additionally imaged in connection with an ROI (operation S510), if the partial imaging mode is selected.

A second image according to an exemplary embodiment may include the portion determined in operation S510.

The determining of a portion to be additionally imaged in connection with an ROI (operation S510) may include estimating a portion of an ROI that is not included in the first image (operation S511) and determining an additional imaging area that includes the estimated portion, by using size information of the first image (operation S513).

An imaging condition according to the partial imaging mode may be selected based on the portion that is estimated in operation S510 (operation S630), and a second image of the object may be obtained according to the selected imaging condition (operation S700).

The estimating of a portion of an ROI that is not included in the first image (operation S511) may include determining a size and a position of the portion not included in the first image based on a size and a position of an ROI included in a reference image.

The size information of the first image according to an exemplary embodiment may include at least one of height information and width information of the first image.

Figure 12A:
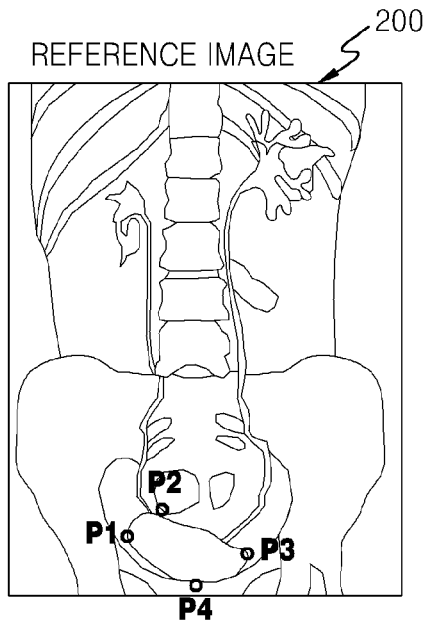
FIGS. 12A and 12B show an estimation of a portion to be additionally imaged, according to an exemplary embodiment.
Figure 12B:
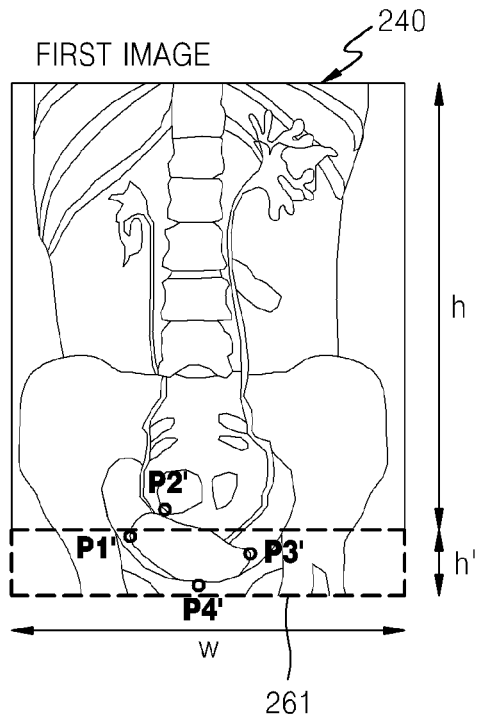
Figure 13A:
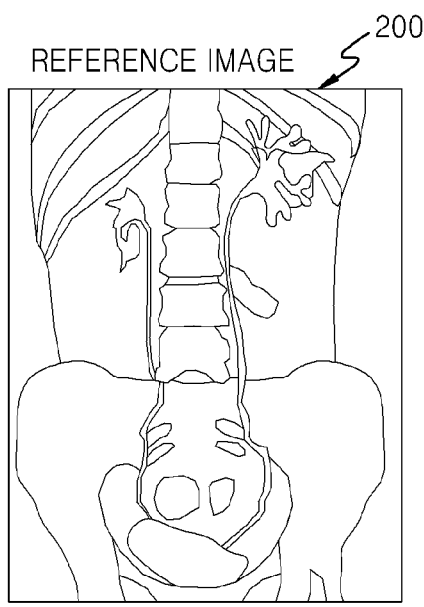
FIGS. 13A and 13B show an estimation of a portion to be additionally imaged, according to an exemplary embodiment.
Figure 13B:
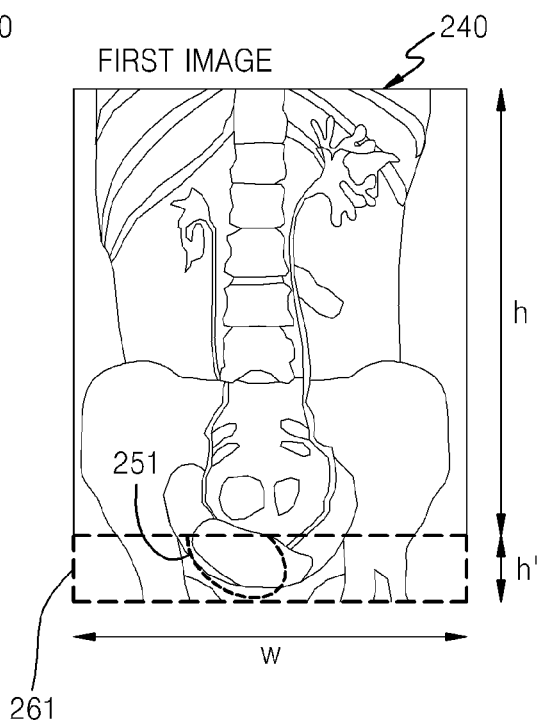

The determining an additional imaging area (operation S513) may include determining an imaging area such that all of ROIs corresponding to the size and the position determined in operation S512 are included in an X-ray image, based on at least one of the height information and the width information of the first image. FIGS. 12A and 12B show an estimated example of a portion to be additionally imaged, according to an exemplary embodiment. FIGS. 13A and 13B show an estimated example of a portion to be additionally imaged, according to an exemplary embodiment.

FIG. 12A illustrates a reference image 200 of a lower abdominal portion of an object, and FIG. 12B illustrates a first image 240 of the lower abdominal portion of the object.

Whether an ROI of the object is included in the first image 240 may be determined by comparing a plurality of feature points of the reference image 200 (e.g., P1 through P4) and a feature point P1' included in the first image 240.

As illustrated in FIG. 12B, for example, some (P1', P3', and P4') of a plurality of feature points P1' through P4' corresponding to a plurality of feature points P1 through P4 of a bladder of the reference image are not included in the second image 240, and accordingly, it may be determined that the entirety or a part of a bladder is not included in the first image 240.

According to an exemplary embodiment, a position and a size of a portion not included in the first image 240 (e.g., feature points P1', P3', and P4') of an ROI of the reference image defined by the plurality of feature points P1 through P4 may be estimated.

Also, according to an exemplary embodiment, an additional imaging area 261 including the portion estimated in operation S512 may be determined by using size information of the first image 240. For example, the additional imaging area 261 may be determined such that it includes all portions that are estimated as not being included in the first image 240 (e.g., portions defined by the feature points P1', P3', and P4').

A height and a width of the additional imaging area 261 may be determined based on the size information of the first image 240. In other words, the additional imaging area 261 may be determined such that it includes all portions of an ROI corresponding to the size and the position determined in operation S512 based on at least one of the height information and the width information of the first image 240.

For example, when a height of the first image 240 from an upper end to a lower end thereof in a vertical direction is h, a height h' of the additional imaging area 261 may be determined from a lower limit of the height h of the first image 240 such that the feature point P4 is included in the additional imaging area 261.

Also, when a horizontal size of the first image 240 from the left to the right is referred to as a width w, a width of the additional imaging area 261 may be determined such that the width of the additional imaging area 261 is included in the width w of the first image 240. Alternatively, the width of the additional imaging area 261 may be determined such that it is greater or smaller than the width w of the first image 240.

According to an exemplary embodiment, a portion not included in the first image 240 (e.g., a portion 251 in FIG. 13B) may be estimated by using a boundary line of an ROI.

For example, the portion 251 not included in the first image 240 may be estimated by comparing a boundary line of an ROI included in the reference image 200 and a boundary line obtained from the first image 240.

The additional imaging area 261 including the portion 251 that is lacking in the first image 240 may be determined based on the size information of the first image 240 and the boundary line of an ROI included in the reference image 200. As described above, the additional imaging area 261 including the portion 251 lacking in the first image 240 may be determined by using at least one of the height h and the width w of the first image 240.

Figure 14:
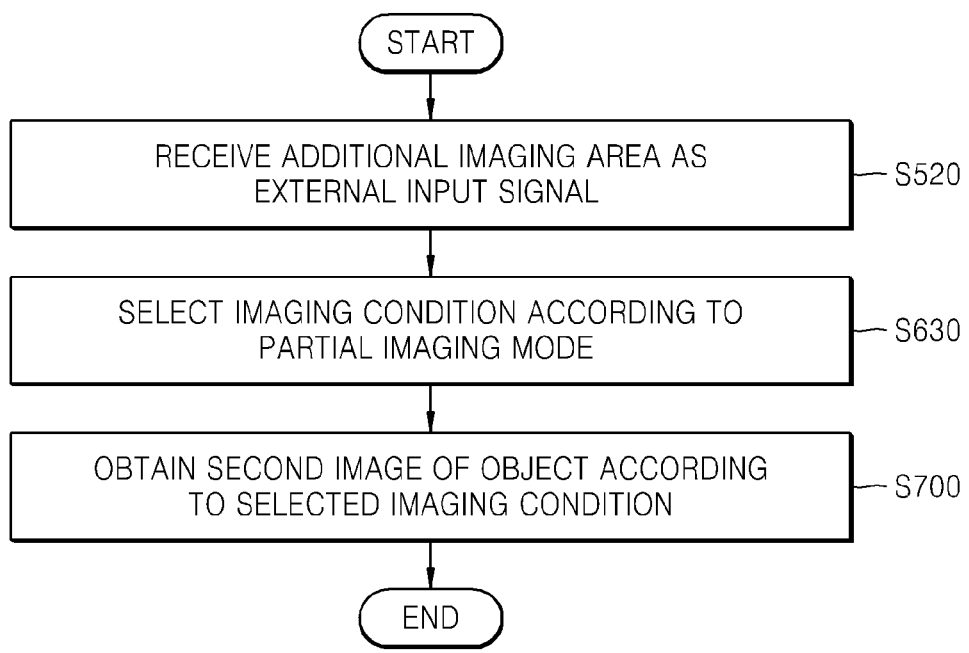
FIG. 14 is a flowchart illustrating a method of determining a portion to be additionally imaged, when a partial imaging mode is selected, according to an exemplary embodiment.

FIG. 14 is a flowchart illustrating a method of determining a portion to be additionally imaged, when a partial imaging mode is selected, according to an exemplary embodiment.

The method according to an exemplary embodiment may further include receiving an additional imaging area of an object, as an external input signal (operation S520), when a partial imaging mode is selected.

A second image corresponding to the additional imaging area received as an external input signal may be obtained.

The method according to an exemplary embodiment may further include setting an imaging condition based on the selected imaging mode (operation S630). That is, in operation S630, an imaging condition according to the partial imaging mode may be selected based on the additional imaging area received from the outside in operation S520.

The imaging condition may include at least one of, for example, an X-ray radiation intensity, a position of an X-ray source, an amount of collimation (e.g., a range of radiation determined by at least one of a position and a size of a collimator), a position of an X-ray detector, and an image resolution.

Also, obtaining a second image (operation S700) according to an exemplary embodiment may include obtaining an X-ray image of an object according to the imaging condition set in operation S630. That is, the second image may be obtained according to the imaging condition selected in operation S630.

Figure 15A:
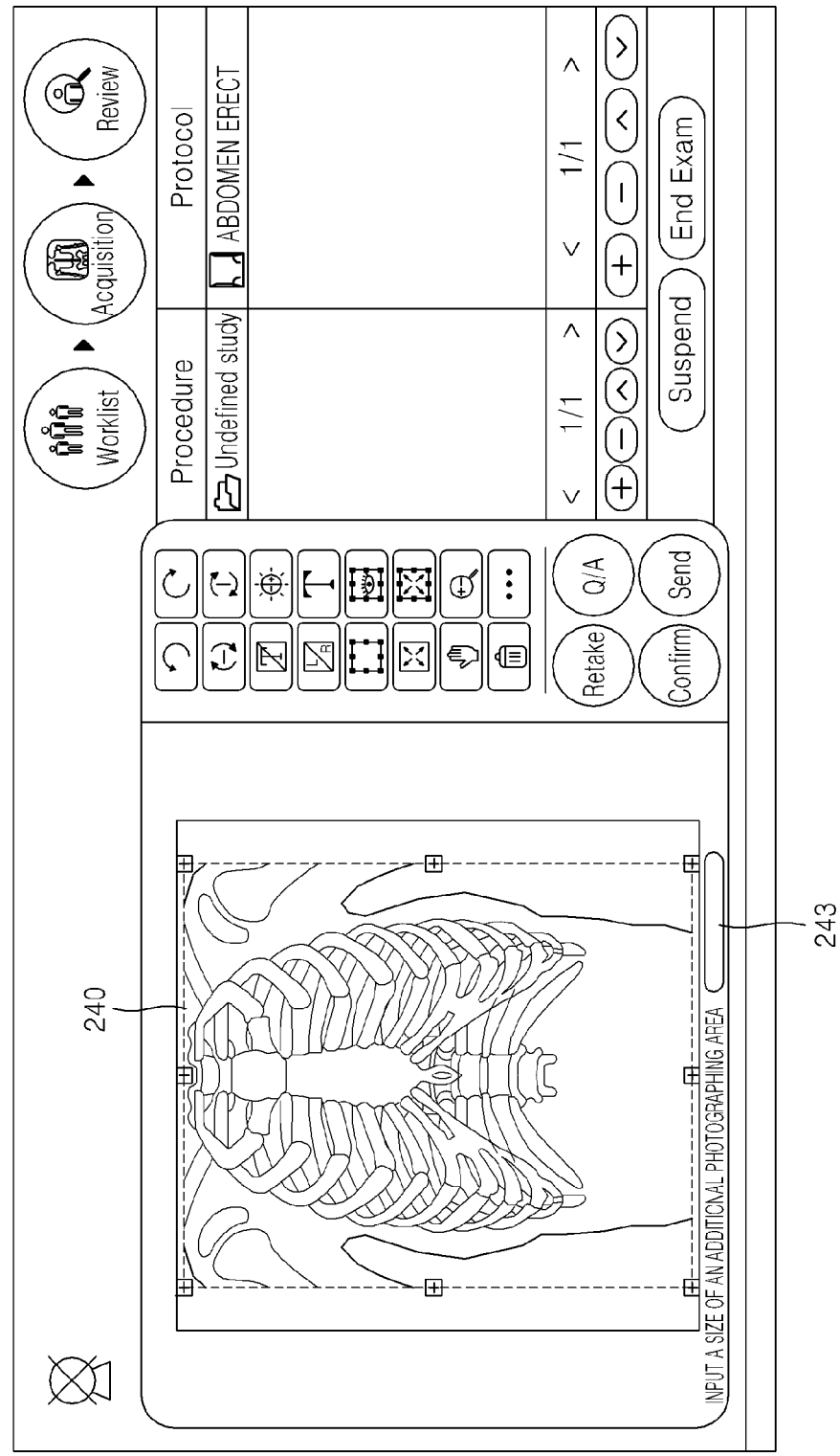
FIGS. 15A, 15B, and 15C illustrate examples, in which a portion to be additionally imaged is received as an external input signal, according to an exemplary embodiment.
Figure 15B:
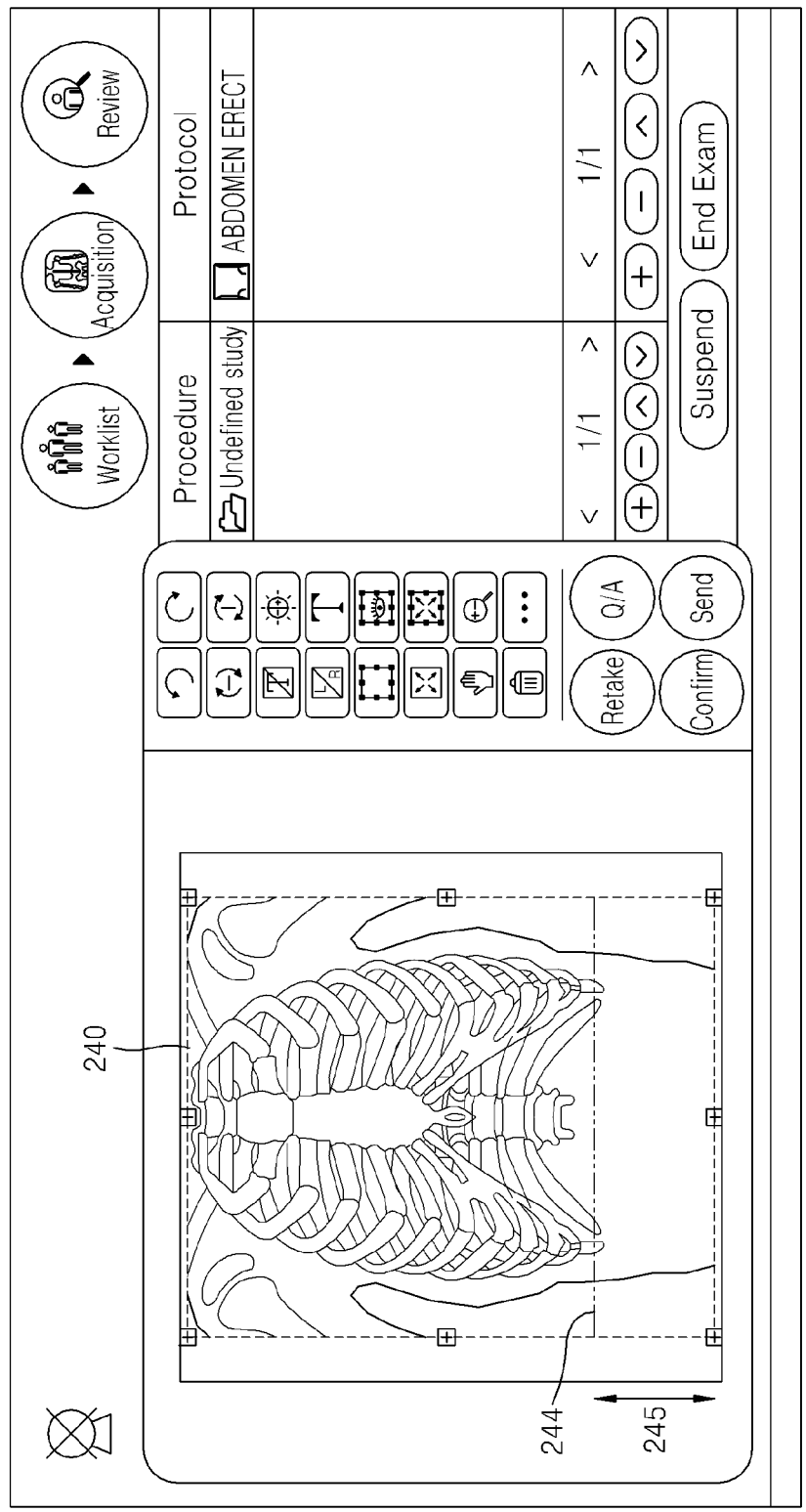
Figure 15C:
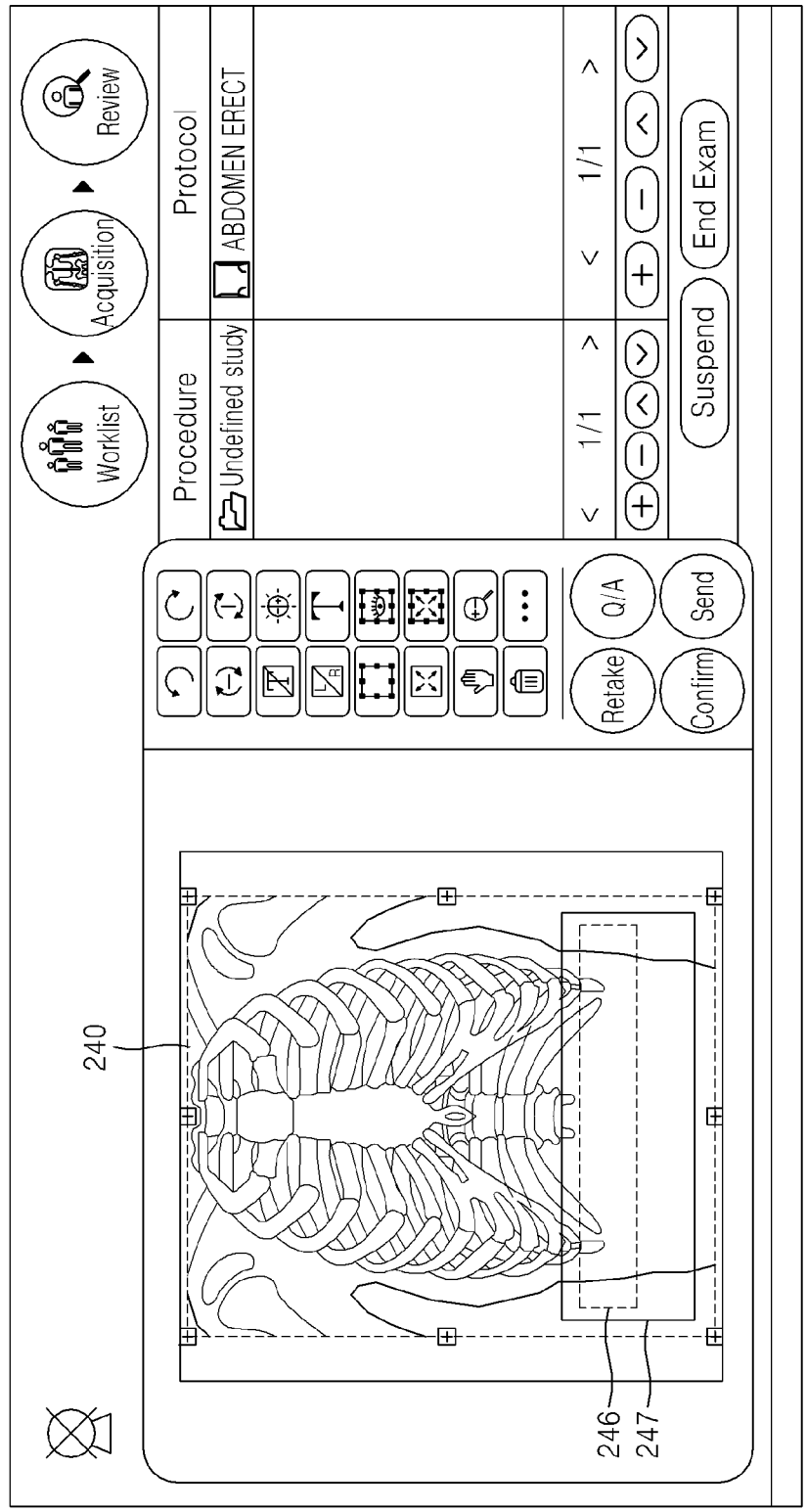

FIGS. 15A, 15B, and 15C illustrate an example, in which a portion to be additionally imaged is received as an external input signal, according to an exemplary embodiment.

An interface 243 through which an additional imaging area is to be received may be provided via a screen on which a first image 240 of an object is displayed. As illustrated in FIG. 15A, the interface 243 may be provided as a form through which a value of an additional imaging area is to be directly input by a user (e.g., a figure input window) or as an image form on which previously set exemplary values of an additional imaging area (e.g., width (w)×height (h), i.e., 14(inch)×1(inch), 14(inch)×2(inch), 12(inch)×1(inch), etc.) including at least one of a character, a number, and an icon are included. The previously set exemplary values may be provided to the user in the form of a pull-down menu. A user may select one of the provided values of the pull down menu. For example, a portion to be additionally imaged may be estimated based on a size of a reference image. A portion to be additionally imaged may be determined based on a size of an image that is estimated so that image includes the entire ROI.

In addition, a signal regarding an additional imaging area may be received as sound such as a user's voice, via a microphone or the like.

Also, as illustrated in FIG. 15B, the user may set an additional imaging area via an input for manipulating the sliding bar 244 in an upward or downward direction indicated by an arrow 245.

Also, as illustrated in FIG. 15C, the user may set an additional imaging area via an input for reducing or extending a size of an adjustable window 246 which may be larger or smaller than the additional imaging area. Also, in order to obtain a precise second image including a portion that is lacking in the first image 240, an area that is to be potentially overlapped, for example, an area 247, may be extended. For example, the area 247 may be extended on a screen that displays the first image 240 illustrated in FIGS. 15A through 15C. The area 247 may be extended by being popped up on the screen that displays the first image 240 or by being displayed on another screen as a different layer so that the user may easily observe the area 247.

Although an additional imaging area is illustrated in a lower portion of the first image 240 in FIGS. 15A through 15C, an exemplary embodiment is not limited thereto. For example, the additional imaging area may be near an upper portion of the first image 240.

Figure 16:
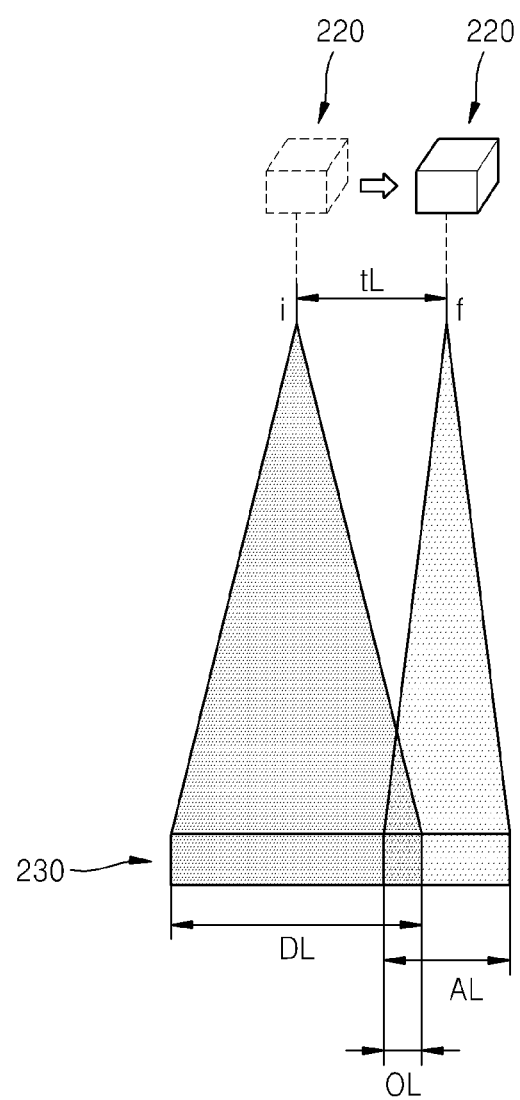
FIG. 16 illustrates an example of selecting an imaging condition according to an exemplary embodiment.

FIG. 16 illustrates an example of selecting an imaging condition, according to an exemplary embodiment.

When an X-ray source 220 according to an exemplary embodiment is a stepping type, an imaging condition regarding a position of the X-ray source 220 may be selected as follows.

An X-ray irradiated at a first position i of the X-ray source 220 may be detected by using an X-ray detector 230 to obtain a first image. As described above, the X-ray source 220 may move to a second position f to correspond to an additional imaging area that is estimated according to an exemplary embodiment or that is determined based on a value received from the outside.

A distance tL that the X-ray source 220 moves may be obtained based on Equation 1 below.

$$tL = (DL + AL)/2 - OL \quad \text{[Equation 1]}$$

The distance tL that the X-ray source 220 has moved corresponds to a difference between the second position f and the first position i, and a length DL of the X-ray detector 230 refers to a length of the X-ray detector 230 that is used in obtaining a first image, and an additional imaging area AL refers to a length corresponding to an imaging area to obtain a second image, and an overlapped length OL may refer to a length by which the first and second images are overlapped.

The overlapped length OL according to an exemplary embodiment may have various values according to ROIs. For example, an amount of exposure to radiation with respect to the object may be minimized by optimizing the overlapped length according to relative template sizes of respective imaged areas. The overlapped length OL according to an exemplary embodiment may be included in a range from, for example, about 35 mm to about 90 mm in consideration of a tube anode heel effect of the X-ray source 220. For example, the overlapped length OL may be 50 mm.

For example, according to an exemplary embodiment, the overlapped length OL may be set to be about 4% of a height value of the second image. For example, when the height value of the second image is 1125 mm, the overlapped length OL may be 45 mm. The overlapped length OL may be set such that a cumulative dose of radiation with respect to the object is minimized.

Also, according to an exemplary embodiment, to obtain a second image, the X-ray detector 230 may move according to the additional imaging area AL in one of an upward direction, a downward direction, a direction to the left, a direction to the right, and a diagonal direction. At least one of the X-ray source 220 and the X-ray detector 230 may be moved automatically or manually according to a selected imaging mode.

The X-ray source 220 may be a stationary X-ray source, and the object may be located on a table (not shown). The table may be moved by using a driving mechanism (not shown) to obtain an image of a predetermined portion of the object (for example, a lacking portion of an ROI). An X-ray detector may be embedded in the table or disposed under the table. The X-ray detector may be disposed separately from the table or may be moved automatically or manually according to a selected imaging mode.

Figure 17:
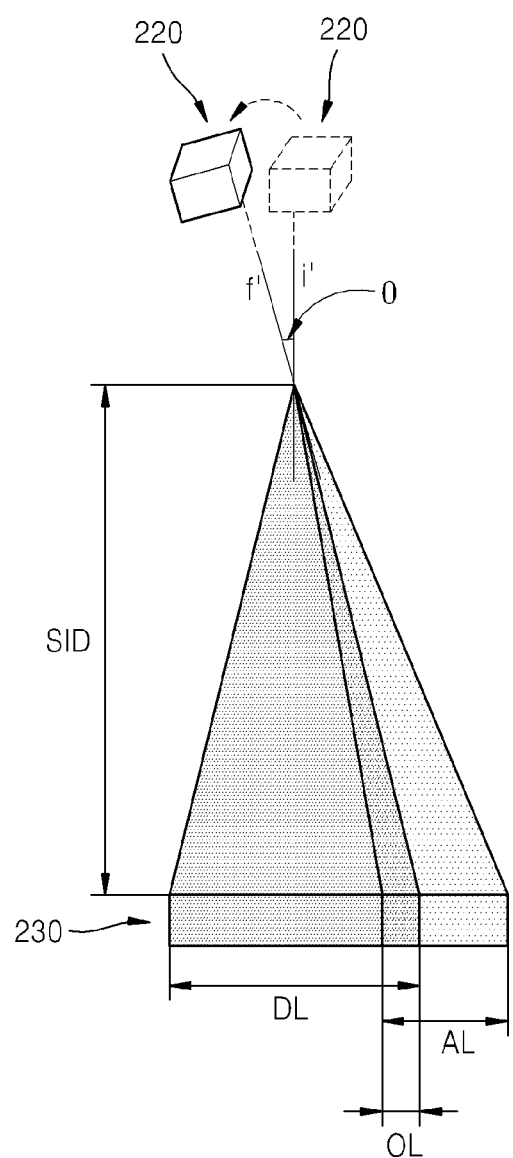
FIG. 17 illustrates an example of selecting an imaging condition according to an exemplary embodiment.

FIG. 17 illustrates an example of selecting an imaging condition, according to an exemplary embodiment.

When an X-ray source 220 according to an exemplary embodiment is a rotation type, an imaging condition regarding a position of the X-ray source 220 may be selected as follows.

An X-ray irradiated at a first position i' of the X-ray source 220 may be shown as a first image through the X-ray detector 230. The X-ray source 220 may be rotated by a predetermined angle (θ) to be moved to a second position f' so as to correspond to an additional imaging area that is estimated according to an exemplary embodiment or that is determined based on a value received from the outside, as described above. In this case, the rotational angle (θ) of the X-ray source 220 may refer to an angle between the second position f' and the first position i'.

The rotational angle (θ) of the X-ray source 220 may be obtained based on Equations 2 and 3 below.

$$\theta = \tan^{-1}\left(\frac{IL}{SID}\right) \quad \text{[Equation 2]}$$

$$IL = (DL + AL)/2 - OL \quad \text{[Equation 3]}$$

IL may refer to a rotational movement distance of the X-ray source 220 formed by rotating the X-ray source 220, and SID may refer to a distance between the X-ray source 220 and an X-ray image. An X-ray image is obtained from data detected by using the X-ray detector 230, and thus, SID may include, for example, a distance between the X-ray source 220 and the X-ray detector 230.

An X-ray irradiation angle according to rotation of the X-ray source 220 may be included in a range from about 12% to about 15% with respect to the entire allowable range of the X-ray irradiation angle. The X-ray irradiation angle may be adjusted to be about 12% with respect to the entire allowable range of the X-ray irradiation angle.

A length DL of the X-ray detector 230 may refer to a length of the X-ray detector 230 used in obtaining the first image, and an additional imaging area AL may refer to a length corresponding to an imaging area to obtain the second image, and an overlapped length OL may refer to a length by which the first and second images are overlapped.

The overlapped length OL according to an exemplary embodiment may have various values according to ROIs. For example, an amount of exposure to radiation with respect to the object may be minimized by optimizing the overlapped length according to relative template sizes of respective imaged areas. The overlapped length OL according to an exemplary embodiment may be included in a range from, for example, about 35 mm to about 90 mm in consideration of a tube anode heel effect of the X-ray source 220. The overlapped length OL may be 50 mm. For example, according to an exemplary embodiment, the overlapped length OL may be set to be about 4% of a height value of the second image. For example, when the height value of the second image is 1125 mm, the overlapped length OL may be 45 mm. The overlapped length OL may be set such that a cumulative dose of radiation with respect to the object is minimized.

Figure 18:
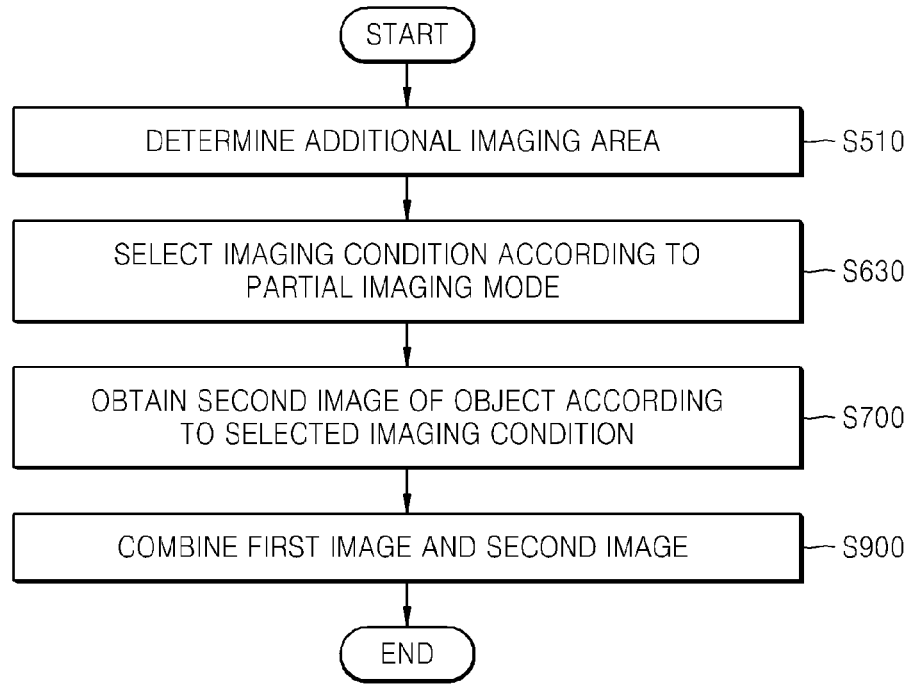
FIG. 18 is a flowchart illustrating a method of combining a first image and a second image, according to an exemplary embodiment.

FIG. 18 is a flowchart illustrating a method of combining a first image and a second image, according to an exemplary embodiment.

The method according to an exemplary embodiment may further include combining the first image and the second image (operation S900).

For example, when a partial imaging mode is selected, an additional imaging area may be determined (operation S510), and an imaging condition according to the partial imaging mode may be selected based on the determined additional imaging area (operation S630), and a second image of an object may be obtained according to the selected imaging condition (operation S700). The first image and the second image may be combined by using a predetermined image combining method (operation S900). This will be described later with reference to FIG. 20.

Figure 19:
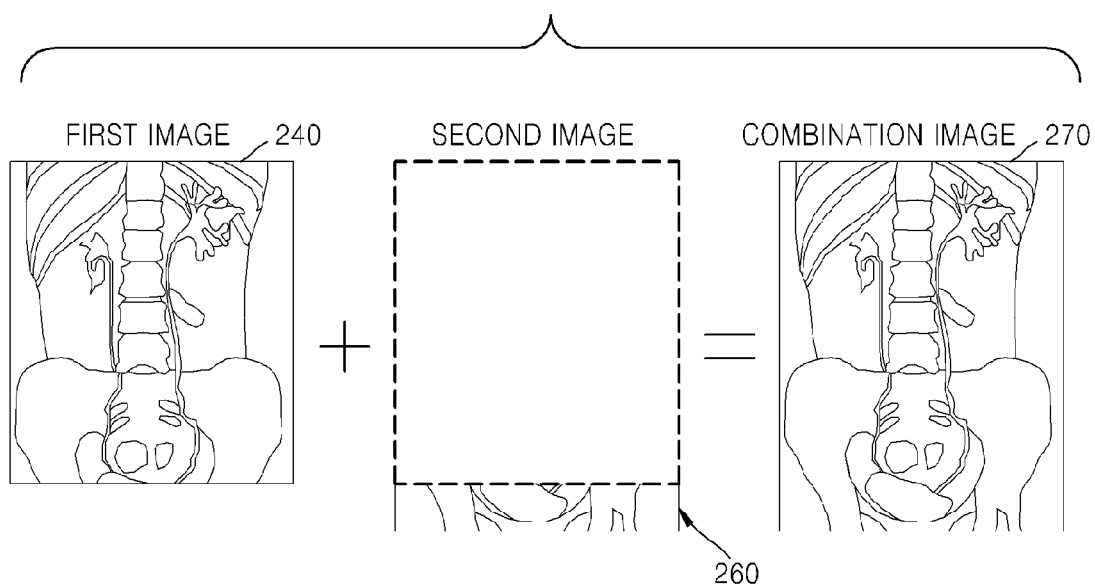
FIG. 19 illustrates an example of combining a first image and a second image, according to an exemplary embodiment.

FIG. 19 illustrates an example of combining a first image 240 and a second image 260, according to an exemplary embodiment.

A combination image 270 may be obtained by applying a predetermined image combining technique to the first image 240 and the second image 260. As described above, the combination image 270 may be an image including an ROI of an object.

Figure 20A:
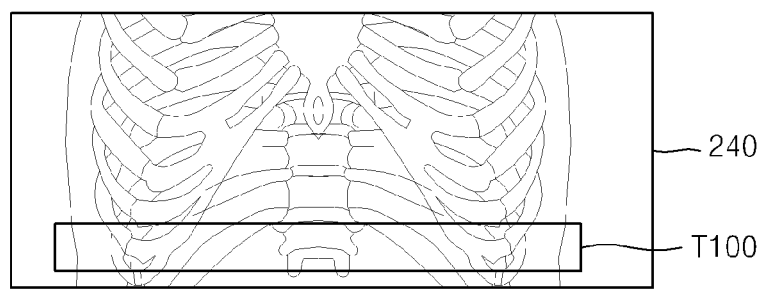
FIGS. 20A and 20B illustrate an example of combining a first image and a second image, according to an exemplary embodiment.
Figure 20B:
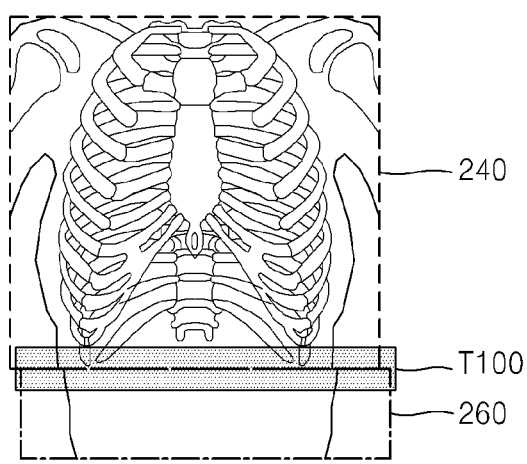

FIGS. 20A and 20B illustrate an example of combining a first image 240 and a second image 260, according to an exemplary embodiment.

According to an exemplary embodiment, images may be combined by using at least one template. Matching of a plurality of images refers to stitching an image (for example, a reference image) and another image (for example, a stitching image) together. A search area may be provided in the reference image, and a template may be provided in the stitching image. In other words, matching of a plurality of images may refer to a process of determining a matching condition of a stitching image with respect to a reference image (for example, determining a movement distance of X coordinates or Y coordinates of an image or a rotational angle of an image). For example, a temperate such as a template T100 refers to a predetermined area in a stitching image, for which a condition for matching with respect to a plurality of images is searched for, and may have various shapes such as a template to which weights are applied to respective major ROIs or a single template. A matching condition such as a movement distance or an angle of a stitching image with respect to a reference image may be searched for by using the template to match the plurality of images.

A template (e.g., a template T100) may refer to an area in an image of an object, defined by a predetermined position or a predetermined size. The template (e.g., a template T100) may refer to the entire image or a portion of an image of an object. The template (e.g., a template T100) may be used as a reference area for stitching a plurality of images.

The template T100 having a predetermined size at a predetermined position of the first image 240 may be set. A combination image 270 may be obtained by performing template matching with respect to the first image 240 and the second image 260 based on the template T100.

For example, when the template T100 having a predetermined size at a predetermined position of the first image 240 is set, a portion corresponding to the template T100 may be detected from the second image 260. For example, a portion included in the second image 260 that has a large similarity to the template T100 may be detected from the second image 260.

A second image according to an exemplary embodiment may include at least one template to be used in combining the second image with the first image. The at least one template included in the second image may correspond to at least one template with respect to the first image. For example, at least one template set with respect to the second image may be matched to the at least one template set with respect to the first image.

The combining of the first and second images according to an exemplary embodiment (operation S900) may include stitching (or matching) the second image to the first image by using at least one template.

For example, the first image and the second image may be stitched based on at least one template with respect to the first image or based on at least one template with respect to the second image. Alternatively, the first image and the second image may be stitched by using respective templates of the first and second images.

A position and a size of at least one template according to an exemplary embodiment may be set in various ways. That is, at least one template according to an exemplary embodiment may be set differently based on at least one of properties of an object, a size of an ROI, and a position of an ROI.

The properties of the object according to an exemplary embodiment may include the age, gender, height, weight, body type, a part to be imaged, and medical history of the object.

The second image according to an exemplary embodiment may include a plurality of templates to be used in combining the second image with the first image. The combining of the first and second images (operation S900) may include applying different weights to a plurality of templates and stitching the first and second images based on the applied weights.

Figure 21A:
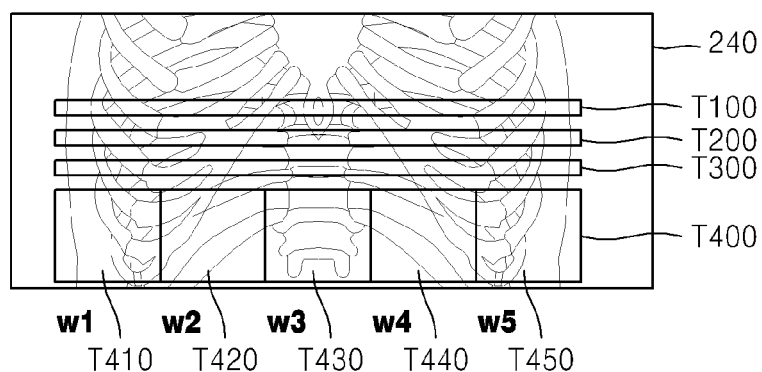
FIGS. 21A and 21B illustrate an example of combining a first image and a second image, according to an exemplary embodiment.
Figure 21B:
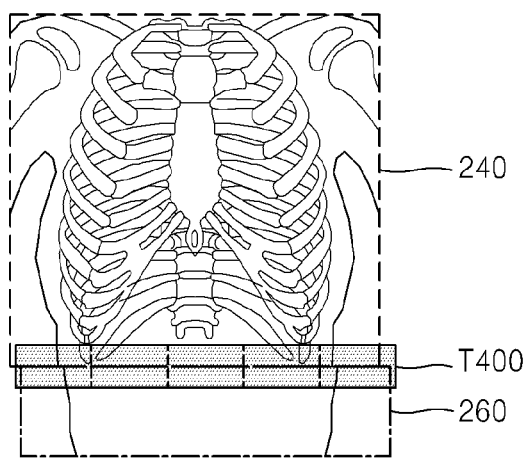

FIGS. 21A and 21B illustrate an example of combining a first image and a second image, according to an exemplary embodiment.

According to an exemplary embodiment, a plurality of different templates T100, T200, T300, T400 may be set with respect to a first image 240. Also, similarly, a plurality of different templates may be set with respect to a second image 260.

A template in the form of a block that has a fixed size and is set at a fixed position may be vulnerable to a reversion phenomenon between images, particularly, in imaging an object using an X-ray source of a stepping type, and thus, it may be difficult to obtain an exact X-ray image of an object. Also, when a template in the form of a block that has a fixed size and is set at a fixed position is used, if the object moves or image quality of an obtained image of the object is not uniform, efficiency of image stitching may decrease.

According to an exemplary embodiment, at least one of a position and a size of a template may be variably set based on a feature point or a boundary line of an ROI of an object. For example, at least one of a position and a size of a template may be set such that the template includes a feature point of an ROI of an object included in the first image 240 (e.g., a feature point P2' of FIG. 12B).

The template according to an exemplary embodiment may be set to have a predetermined size at a position that is nearest to the feature point included in the first image 240 (e.g., a feature point P2' of FIG. 12B), but is not limited thereto.

Also, as illustrated in FIG. 21A, the template T400 according to an exemplary embodiment may include at least one sub-template (e.g., T410 through T450).

According to an exemplary embodiment, different weights may be applied to a plurality of sub-templates (e.g., T410 through T450).

For example, different weights may be respectively applied to sub-templates, such that a weight W1 is applied to a template T410, and a weight W2 is applied to a template T420. For example, weights W1 through W5 applied to a plurality of sub-templates may be different from one another. Also, some of sub-templates may have the same weight, which is different from those of other sub-templates (for example, W1=W4=5 and W1<W2<W3), but an exemplary embodiment is not limited thereto.

According to an exemplary embodiment, by using the plurality of templates T410 through T450 to which weights are applied, the first image 240 and the second image 260 may be stitched. Image stitching is performed based on the above-described applied weights a data amount to be processed during image stitching may be reduced, and thus, a combination image may be quickly obtained, and an imaging time may be reduced.

For example, elements of an image area (e.g., a pixel value) included in a template to which a relatively high weight (e.g., W3 in the above-described example) is applied may be used frequently in image stitching. On the other hand, elements of an image area included in a template to which a relatively low weight is applied may be considered relatively little in image stitching.

The first image 240 and the second image 260 may be stitched smoothly and naturally through a blending operation. Blending between images may include an operation of adjusting a mixing ratio between a first image and a second image near an image stitching portion to express the image stitching portion smoothly and naturally.

A series of processes to appropriately match the first image 240 and the second image 260 may be additionally performed by cropping a portion or the entirety of each of the first and second images 240 and 260 or rotating the first and second images 240 and 260 or adjusting phases of the first and second images 240 and 260.

Figure 22:
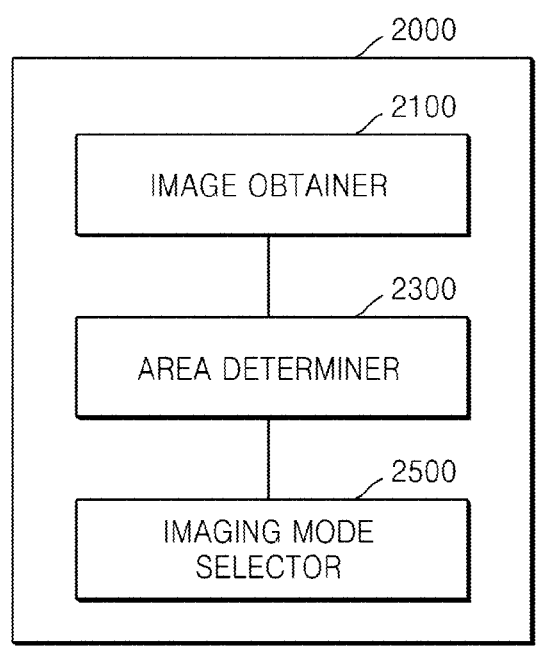
FIG. 22 is a block diagram illustrating an apparatus for obtaining an X-ray image including an ROI of an object, according to an exemplary embodiment.

FIG. 22 is a block diagram illustrating an apparatus 2000 for obtaining an X-ray image including an ROI of an object according to an exemplary embodiment.

The apparatus 2000 for obtaining an X-ray image of an ROI of an object may include an image obtainer 2100 for obtaining a first image of an object, an area determiner 2300 for determining whether the first image includes an ROI, and an imaging mode selector 2500 for selecting an imaging mode to re-image an object based on a result of determination by the area determiner 2300.

The image obtainer 2100 may obtain a first X-ray image 240 of an object 210 located between an X-ray source 220 and an X-ray detector 230. For example, while a user intends to obtain a first X-ray image 240 including all of a kidney 11, a ureter 13, and a bladder 15 of an object, all or a portion of a bladder 15 may be not included in the first X-ray image 240. For example, the first image may be analyzed in order to reduce a degree of exposure of the object to radiation, and an imaging mode may be selected, in which a second image including a portion lacking in the first image is imaged. The above operations may be performed on an object existing at a predetermined position, and the first image of the object existing at the predetermined position may be a reference for selecting an imaging mode.

The imaging mode may be selected from a plurality of imaging modes corresponding to imaging areas having different sizes. The plurality of imaging modes may include an entire ROI imaging mode and a partial imaging mode.

The area determiner 2300 may determine whether an ROI is included in a first image by comparing a reference image of an object and the first image. An operation of comparing images according to an exemplary embodiment may include a series of operations to determine similarity between a plurality of images.

The imaging mode selector 2500 may select an imaging mode to re-image an object based on a result of the determination by the area determiner 2300.

Also, according to an exemplary embodiment, a second image of the object may be obtained by using the image obtainer 2100 according to the imaging mode selected by using the imaging mode selector 2500, and the second image may include a portion or the entirety of an ROI.

The area determiner 2300 according to an exemplary embodiment may compare the reference image of the object and the first image.

The reference image may be selected from previously stored images based on properties of the object. The reference image of the object may be statistically determined according to a portion of the object and stored in a database in advance.

For example, predetermined elements found in X-ray images of a chest of a plurality of objects (e.g., the number of ribs or positions of diaphragms included in the images) are extracted, and the plurality of apparent elements may be defined as common features based on a frequency with which predetermined elements extracted from the X-ray images of the chest of the plurality of objects appear, and the X-ray images of the chest of the objects including the common features may be defined as reference images and stored.

In addition, the reference images according to an exemplary embodiment may be selected from images of the plurality of objects stored in advance, based on properties of an object that is to be imaged. The properties of the object according to an exemplary embodiment may include the age, gender, height, weight, body type, part to be imaged, and medical history of the object that is to be imaged, as described above.

Figure 23:
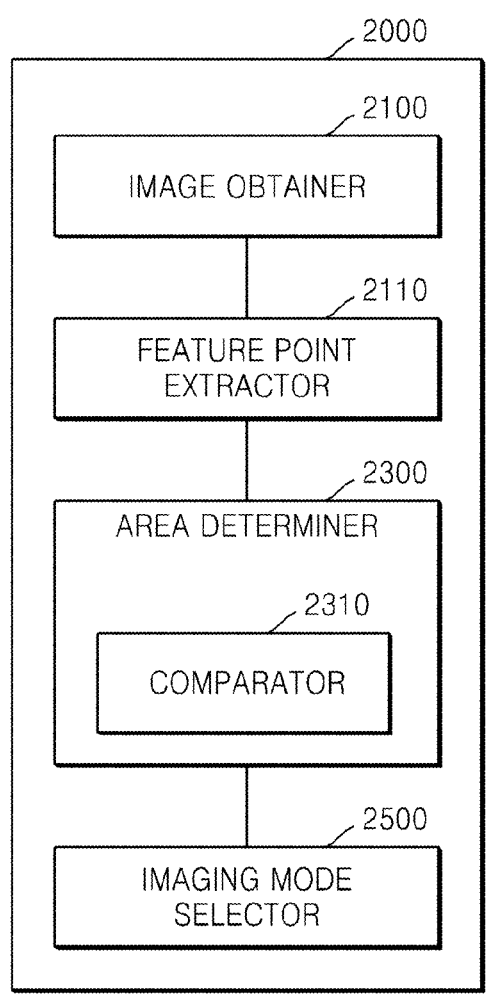
FIG. 23 is a block diagram illustrating an apparatus for obtaining an X-ray image including an ROI of an object, according to an exemplary embodiment.

FIG. 23 is a block diagram illustrating an apparatus 2000 for obtaining an X-ray image including an ROI of an object, according to an exemplary embodiment.

The apparatus 2000 according to an exemplary embodiment may further include a feature point extractor 2110 for extracting at least one feature point related to an ROI, from an obtained first image, and an area determiner 2300 may further include a comparator 230 comparing a feature point extracted from the first image by using the feature point extractor 2110 with a feature point of an ROI included in a reference image.

Whether the first image includes an ROI may be determined by using a SIFT method in which a feature point of an object is used or by using a model-based matching method.

The number and a position of at least one feature point may be defined in advance according to a size and a position of an ROI according to an exemplary embodiment.

The feature point according to an exemplary embodiment may include a predetermined point to distinguish, for example, tissues included in an X-ray image of an object. For example, the feature point may be used as an identifier to identify at least one of a shape, size, and position of a tissue or the like included in an X-ray image of an object.

As illustrated in FIG. 7A, for example, a plurality of feature points (e.g., feature points P1 through P5) may indicate that an image includes a skull of an object. That is, the skull of the object may be identified in an X-ray image based on a plurality of feature points (e.g., feature points P1 through P5).

Also, referring to FIGS. 7B through 7E again, at least one feature point of each portion of an object may be determined in advance.

The comparator 2310 may compare the number and a position of a feature point of the ROI included in the reference and the number and a position of a feature point extracted from the first image. The area determiner 2300 may determine whether the first image includes an ROI of an object based on a result of determination by the comparator 2310.

For example, when a skull of an object is an ROI, and only some feature points (e.g., P1', P2', and P5') are found in the first image that is obtained in order to capture an image of the skull of the object, feature points (e.g., P3' and P4') of the first image corresponding to the feature points P3 and P4 from a plurality of feature points (e.g., P1 through P5) included in the reference image do not exist. Thus, it may be determined that the first image does not include an ROI. That is, a lower jaw corresponding to the feature points P3 and P4 of the reference image may be determined as being not included in the first image.

Figure 24:
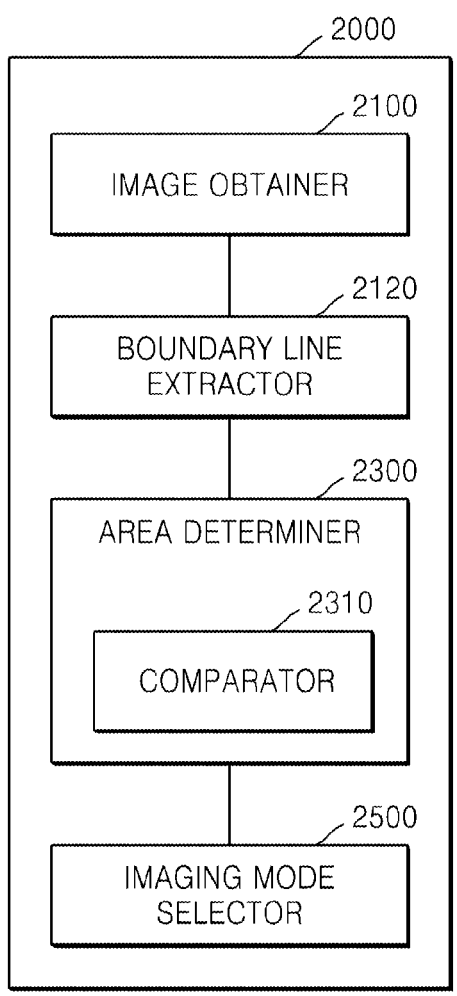
FIG. 24 is a block diagram illustrating an apparatus for obtaining an X-ray image including an ROI of an object, according to an exemplary embodiment.

FIG. 24 is a block diagram illustrating an apparatus for obtaining an X-ray image including an ROI of an object, according to an exemplary embodiment.

The apparatus 2000 may further include a boundary line extractor 2120 extracting a boundary line of an ROI from an obtained first image and a comparator 2310 comparing the boundary line extracted from the first image with a boundary line of an ROI included in a reference image.

Similarly to the feature points, the boundary line according to an exemplary embodiment may include a predetermined line used to distinguish, for example, a tissue included in an X-ray image of an object. The line may be a solid line, a dotted line, or an alternating long and short dashed line, but is not limited thereto. The boundary line may be used as an identifier to identify at least one of a shape, size, and position of the tissue included in the X-ray image of the object.

Referring to FIG. 9A again, for example, a skull of an object may be identified by a boundary line 11. Also, as illustrated in FIGS. 9B through 9E, a boundary line of each portion of the object may be edited and may be determined in advance.

The comparator 2310 may determine a similarity between the boundary line extracted from the first image and the boundary line of the ROI included in the reference image. The area determiner 2300 may determine whether the first image includes an ROI of the object based on a result of the determining of the similarity by the comparator 2310.

For example, the similarity between two boundary lines 11 and 11' may be determined based on whether a boundary line (e.g., 11') extracted from the first image is cut or deformed compared to a boundary line (11) of the ROI included in the reference image, and accordingly, whether the first image includes the ROI may be determined.

For example, when a similarity between the boundary line (e.g., 11) of the ROI included in the reference image and the boundary line (e.g., 11') extracted from the first image is about 95% or greater, it may be determined that the ROI is included in the first image, and when the similarity is less than about 75%, it may be determined that the ROI is not included in the first image. However, a value of the similarity used as a reference for the above determination is not limited thereto.

The imaging mode selector 2500 may select one of an entire ROI imaging mode in which the entire ROI of an object is imaged and a partial imaging mode in which a portion of an ROI of an object is imaged.

Referring to FIG. 10 again, a first image of an object may be obtained by using the image obtainer 2100, and whether the first image includes an ROI may be determined by using the area determiner 2300, and when the first image includes an ROI, imaging may end.

Also, when the area determiner 2300 determines that the first image does not include an ROI, an imaging mode for re-imaging an object may be selected by using the imaging mode selector 2500. The imaging mode may include the entire ROI imaging mode and the partial imaging mode.

For example, when the entire ROI imaging mode is selected, an imaging condition according to the entire ROI imaging mode may be selected. The imaging condition may include at least one of, for example, an X-ray radiation intensity, a position of an X-ray source, an amount of collimation (e.g., a range of radiation determined by at least one of a position and a size of a collimator), a position of an X-ray detector, and an image resolution.

A second image of the target image may be obtained by using the image obtainer 2100 according to the imaging condition selected by using the imaging condition setter 2800.

According to an exemplary embodiment, the partial imaging mode may be selected.

For example, when the partial imaging mode is selected, an imaging condition according to the partial imaging mode may be selected by using the imaging condition setter 2800. As described above, the imaging condition may include at least one of, for example, an X-ray radiation intensity, a position of an X-ray source, an amount of collimation (e.g., a range of radiation determined by at least one of a position and a size of a collimator), a position of an X-ray detector, and an image resolution.

A second image of the object may be obtained by using the image obtainer 2100 according to the imaging condition selected by using the imaging condition setter 2800.

Figure 25:
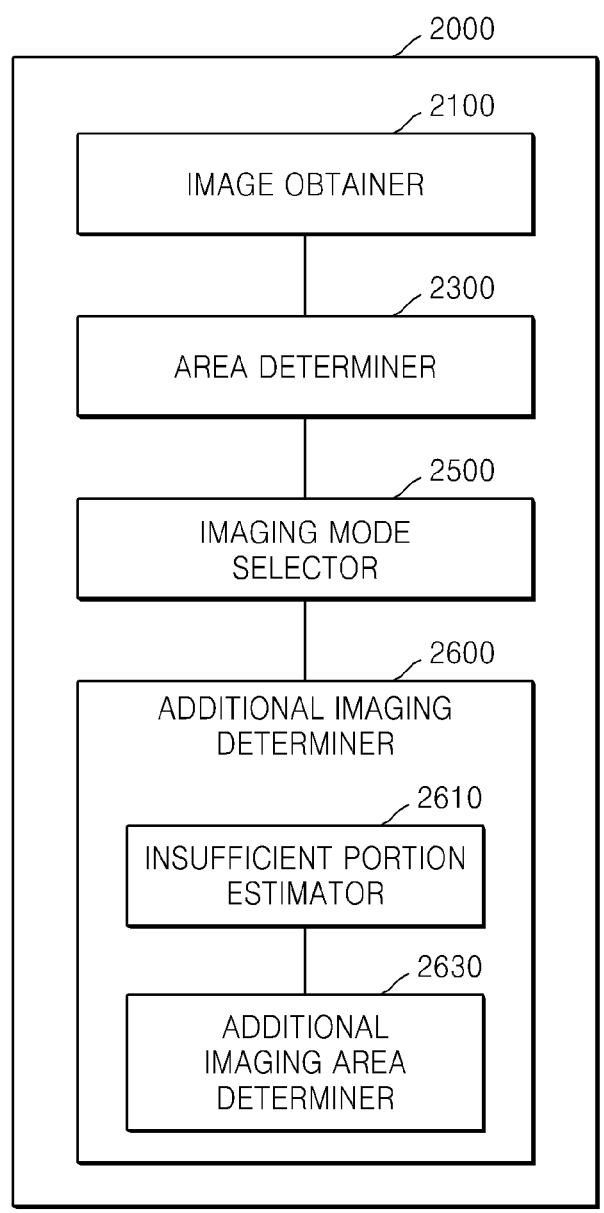
FIG. 25 is a block diagram illustrating an X-ray image obtaining apparatus that further includes an additional imaging determiner, according to an exemplary embodiment.

FIG. 25 is a block diagram illustrating an X-ray image obtaining apparatus 2000 that further includes an additional imaging determiner according to an exemplary embodiment.

The apparatus 2000 may further include an additional imaging determiner 2600 that determines a portion of an ROI that is to be additionally imaged, as a partial imaging mode is selected by using the imaging mode selector 2500. A second image including the portion determined by using the additional imaging determiner 2600 may be obtained.

The additional imaging determiner 2600 according to an exemplary embodiment may include an insufficient portion estimator 2610 that estimates a portion of an ROI not included in the first image and an additional imaging area determiner 2630 that determines an additional imaging area including the portion estimated by using the insufficient portion estimator 2610 by using size information of the first image.

The insufficient portion estimator 2610 may determine a size and a position of a portion not included in the first image based on a size and a position of an ROI included in a reference image.

The size information of the first image according to an exemplary embodiment may include at least one of height information and width information of the first image.

The additional imaging area determiner 2630 may determine an imaging area such that all of portions of an ROI corresponding to the size and the position of the portion determined by using the insufficient portion estimator 2610 are included in the additional imaging area, based on at least one of the height information and the width information of the first image.

Referring to FIGS. 12A and 12B again, FIG. 12A illustrates a reference image 200 of a lower abdominal portion of an object, and FIG. 12B illustrates a first image 240 of the lower abdominal portion of the object.

Whether an ROI of the object is included in the first image 240 may be determined by comparing a plurality of feature points of the reference image 200 (e.g., P1 through P4) and a feature point P1' included in the first image 240. As illustrated in FIG. 12B, for example, when some (P1', P3', and P4') of a plurality of feature points P1' through P4' corresponding to a plurality of feature points P1 through P4 of a bladder of the reference image are not included in the second image 240, it may be determined that the entire or a partial image of the bladder is not included in the first image 240.

According to an exemplary embodiment, a position and a size of a portion not included in the first image 240 (e.g., a portion defined by feature points P1', P3', and P4') in an ROI defined by the plurality of feature points P1 through P4 may be estimated in the reference image.

Also, according to an exemplary embodiment, an additional imaging area 261 including the portion estimated by using the insufficient portion estimator 2610 may be determined by using the additional imaging area determiner 2630 by using size information of the first image 240. For example, the additional imaging area 261 may be determined such that all portions that are estimated as not being included in the first image 240 (e.g., a portion defined by feature points P1', P3', and P4') are included in the additional imaging area 261.

A height and width of the additional imaging area 261 may be determined based on the size information of the first image 240. In other words, the additional imaging area 261 may be determined by using the additional imaging area determiner 2630 such that all portions of an ROI corresponding to the size and position of the portion determined by using the insufficient portion estimator 2610 are included in the additional imaging area 261 based on at least one of the height information and the width information of the first image 240.

For example, when a height of the first image 240 from an upper end to a lower end thereof in a vertical direction is referred to as h, a height h' of the additional imaging area 261 may be determined from a lower limit of the height h of the first image 240 such that the feature point P4' is included.

Also, when a horizontal size of the first image 240 from the left to the right is referred to as a width w, a width of the additional imaging area 261 may be determined such that the width of the additional imaging area 261 is included in the width of the first image 240. Alternatively, the width of the additional imaging area 261 may be determined such that it is greater than the width of the first image 240.

According to an exemplary embodiment, referring to FIG. 13, a portion not included in the first image 240 (e.g., a portion 251 in FIG. 13) may be estimated by using a boundary line of an ROI.

For example, the portion 251 not included in the first image 240 may be estimated by comparing a boundary line of an ROI included in the reference image 200 and a boundary line obtained from the first image 240.

The additional imaging area 261 including the portion 251 that is lacking in the first image 240 may be determined based on the size information of the first image 240 and the boundary line of an ROI included in the reference image 200. As described above, the additional imaging area 261 including the portion 251 lacking in the first image 240 may be determined by using at least one of the height h and the width w of the first image 240.

Figure 26:
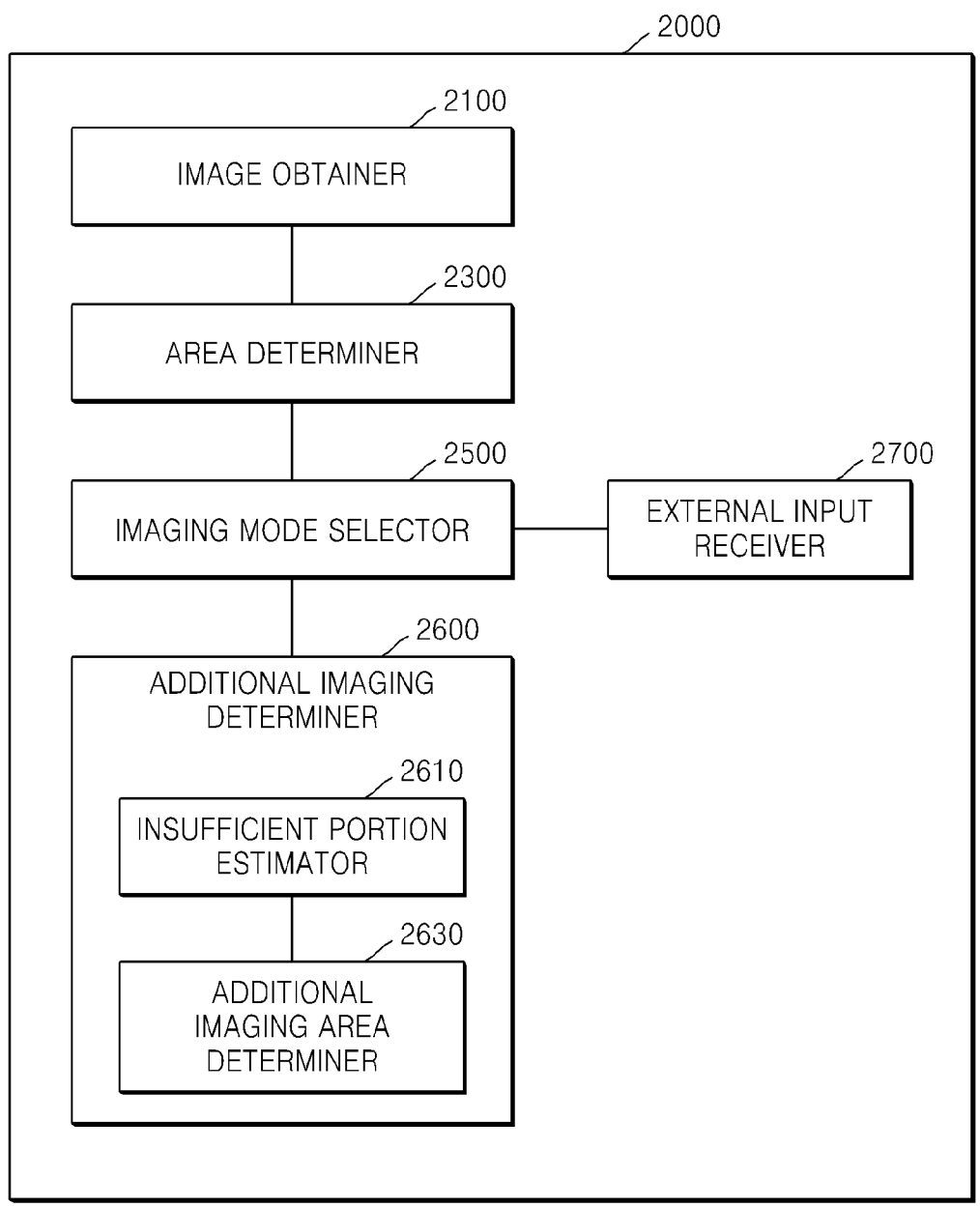
FIG. 26 is a block diagram illustrating an X-ray image obtaining apparatus that further includes an external input receiver and an additional imaging determiner, according to an exemplary embodiment.

FIG. 26 is a block diagram illustrating an X-ray image obtaining apparatus 2000 that further includes an external input receiver and an additional imaging determiner, according to an exemplary embodiment.

The apparatus 2000 may further include an external input receiver 2700 that receives an additional imaging area of an object, as an external input signal, as a partial imaging mode is selected by using the imaging mode selector 2500. A second image corresponding to the additional imaging area received as an external input signal may be obtained.

Figure 27:
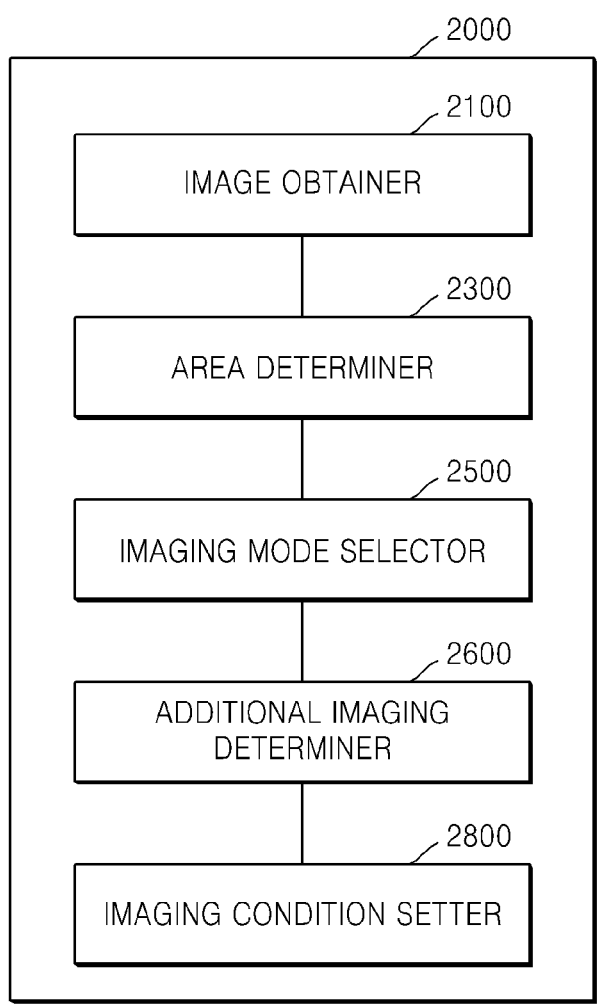
FIG. 27 is a block diagram illustrating an X-ray image obtaining apparatus that further includes an imaging condition setter, according to an exemplary embodiment.

FIG. 27 is a block diagram illustrating an X-ray image obtaining apparatus 2000 that further includes an imaging condition setter 2800, according to an exemplary embodiment.

The apparatus 2000 may further include the imaging condition setter 2800 that sets an imaging condition based on an imaging mode selected by using the imaging mode selector 2500. The second image may be obtained as an X-ray image of an object according to an imaging condition set by using the imaging condition setter 2800.

According to an exemplary embodiment, an imaging condition according to a partial imaging mode may be selected based on an additional imaging area received from the outside by using the external input receiver 2700.

The imaging condition according to an exemplary embodiment may include at least one of a position of an X-ray source, an amount of collimation, a position of an X-ray detector, and an image resolution.

That is, the imaging condition may include at least one of, for example, an X-ray radiation intensity, a position of an X-ray source, an amount of collimation (e.g., a range of radiation determined by at least one of a position and a size of a collimator), a position of an X-ray detector, and an image resolution.

Referring to FIG. 15 again, for example, an interface 243 through which an additional imaging area is to be received may be provided via a screen on which a first image 240 of an object is displayed. As illustrated in FIG. 15, the interface 243 may be provided in a form through which a value of an additional imaging area may be directly input by a user (e.g., a figure input window) or in an image form on which previously set exemplary values of an additional imaging area (e.g., width×height, i.e., 14(inch)×1(inch), 14(inch)×2(inch), 12(inch)×1(inch), etc.) including at least one of a character, a number, and an icon are included. In other words, the external input receiver 2700 may receive an external input that is input via the interface 243 as illustrated in FIG. 15.

A signal regarding an additional imaging area may be received as sound such as the user's voice, via a microphone or the like.

When an X-ray source 220 according to an exemplary embodiment is the stepping type, for example, an imaging condition for a position of the X-ray source 220 may be obtained with reference to FIG. 16 and Equation 1. Also, when the X-ray source 220 is the rotation type, for example, an imaging condition for a position of the X-ray source 220 may be obtained with reference to FIG. 17 and Equations 2 and 3.

Figure 28:
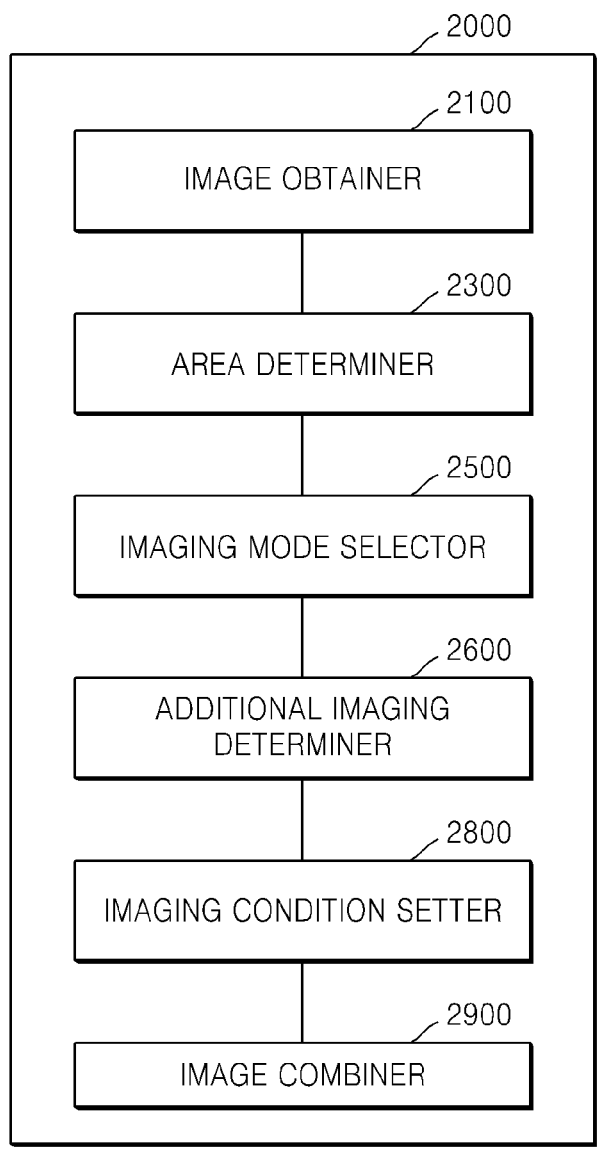
FIG. 28 is a block diagram illustrating an X-ray image obtaining apparatus that further includes an image combiner, according to an exemplary embodiment.

FIG. 28 is a block diagram illustrating the X-ray image obtaining apparatus 2000 that further includes an image combiner 2900, according to an exemplary embodiment.

The apparatus 2000 may further include the image combiner 2900 that combines an obtained first image and an obtained second image.

For example, when the partial imaging mode is selected, an additional imaging area may be determined by using the additional imaging determiner 2600, and an imaging condition according to the partial imaging mode is selected by using the imaging condition setter 2800 based on the determined additional imaging area. The image combiner 2900 may combine the second image and the first image obtained by using the image obtainer 2100 according to the selected imaging condition by using a predetermined image combining method.

According to an exemplary embodiment, images may be combined by using at least one template, as described above.

The image combiner 2900 may set the template T100 having a predetermined size at a predetermined position of a first image 240. A combination image 270 may be obtained by performing template matching with respect to the first image 240 and the second image 260 based on the template T100.

For example, when the template T100 having a predetermined size at a predetermined position of the first image 240 is set, a portion of the first image 240 corresponding to the template T100 may be detected from the second image 260. For example, a portion of the first image 240 that has a large similarity with respect to the template T100 may be detected from the second image 260.

A first image according to an exemplary embodiment may include at least one template to be used in combining the first image with a second image. The second image may include at least one template to be used in combining the second image with the first image.

As described above, at least one template included in the second image may correspond to at least one template with respect to the first image. For example, at least one template with respect to the second image may be set to match at least one template set with respect to the second image.

The image combiner 2900 may stitch an obtained second image with an obtained first image by using at least one template.

For example, the first and second images may be stitched based on at least one template with respect to the first image or at least one template with respect to the second image. Alternatively, the first and second images may be stitched by using respective templates of the first and second images.

A position and size of at least one template according to an exemplary embodiment may be set in various manners. That is, at least one template according to an exemplary embodiment may be set differently based on at least one of properties of an object, a size of an ROI, and a position of an ROI. The properties of the object according to an exemplary embodiment may include the age, gender, height, weight, body type, a part to be imaged, and medical history of the object.

Figure 29:
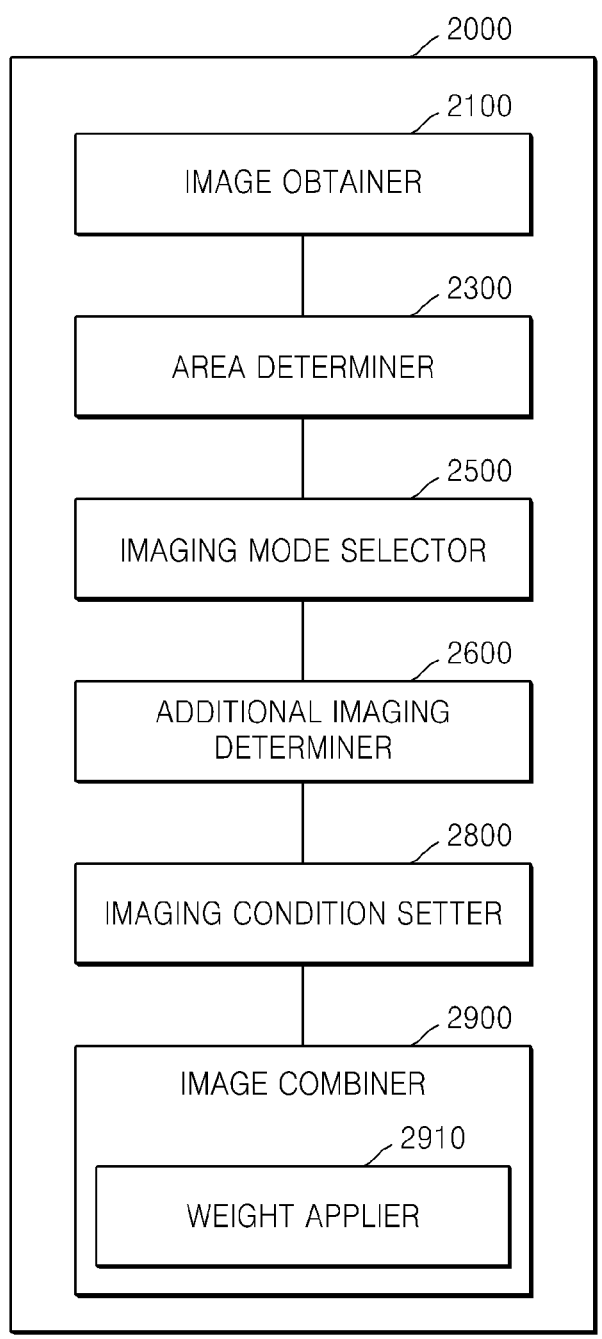
FIG. 29 is a block diagram illustrating an X-ray image obtaining apparatus that further includes an image combiner, according to an exemplary embodiment.

FIG. 29 is a block diagram illustrating an apparatus 2000 that further includes an image combiner 2900, according to an exemplary embodiment.

According to an exemplary embodiment, a second image may include a plurality of templates to be used in combining the second image with a first image.

The image combiner 2900 may further include a weight applier 2910 that applies different weights to a plurality of templates. The image combiner 2900 may stitch an obtained first image and an obtained second image based on weights applied by using the weight applier 2910.

According to an exemplary embodiment, the image combiner 2900 may set a plurality of templates T100 through T400 with respect to the first image 240. Also, similarly, the image combiner 2900 may set a plurality of different templates with respect to the second image 260.

A template in the form of a block that has a fixed size and is set at a fixed position may be vulnerable to a reversion phenomenon between images, particularly, in imaging an object using an X-ray source of a stepping type, and thus, it may be difficult to obtain an exact X-ray image of an object. Also, when a template in the form of a block that has a fixed size and is set at a fixed position is used, if the object moves or image quality of an obtained image of the object is not uniform, efficiency of image stitching may decrease.

According to an exemplary embodiment, at least one of a position and a size of a template may be variably set based on a feature point or a boundary line of an ROI of an object. For example, at least one of a position and a size of a template may be set such that the template includes a feature point of an ROI of an object included in the first image 240 (e.g., a feature point P2' of FIG. 12B). That is, at least one of a position and a size of a template may be set such that the template necessarily includes a feature point included in the first image (e.g., a feature point P2' of FIG. 12B).

A template according to an exemplary embodiment may be set to have a predetermined size at a position nearest to a feature point included in the first image 240 (e.g., a feature point P2' of FIG. 12B), but is not limited thereto.

The template T400 that is set by using the image combiner 2900 according to an exemplary embodiment may include at least one sub-template (e.g., T410 through T450).

According to an exemplary embodiment, different weights may be applied to a plurality of templates (e.g., T410 through T450).

For example, different weights may be respectively applied to sub-templates, for example, such that a weight W1 is applied to a template T410, and a weight W2 is applied to a template T420. For example, weights W1 through W5 applied to a plurality of sub-templates may be different from one another. Also, some of sub-templates may have the same weight, which is different from those of other sub-templates (for example, W1=W4=5 and W1<W2<W3), but the an exemplary embodiment is not limited thereto.

According to an exemplary embodiment, by using the plurality of templates T410 through T450 to which weights are applied by using the weight applier 2910, the first image 240 and the second image 260 may be stitched. Image stitching is performed based on the applied weights as described above as a data amount to be processed during image stitching may be reduced, and thus, a combination image may be quickly obtained, and an imaging time may be reduced.

For example, elements of an image area (e.g., a pixel value) included in a template to which a relatively high weight (e.g., W3 in the above-described example) is applied may be used frequently in image stitching. On the other hand, elements of an image area included in a template to which a relatively low weight is applied may be considered relatively little in image stitching.

According to an exemplary embodiment, the image combiner 2900 may perform an image stitching post-process. For example, the first image 240 and the second image 260 may be stitched smoothly and naturally through a blending operation. Blending between images may include an operation of adjusting a mixing ratio between a first image and a second image near an image stitching portion to express the image stitching portion smoothly and naturally.

A series of processes to appropriately match the first image 240 and the second image 260 may be additionally performed by cropping a portion or the entirety of each of the first and second images 240 and 260, rotating the first and second images 240 and 260, or adjusting phases of the first and second images 240 and 260.

Figure 30:
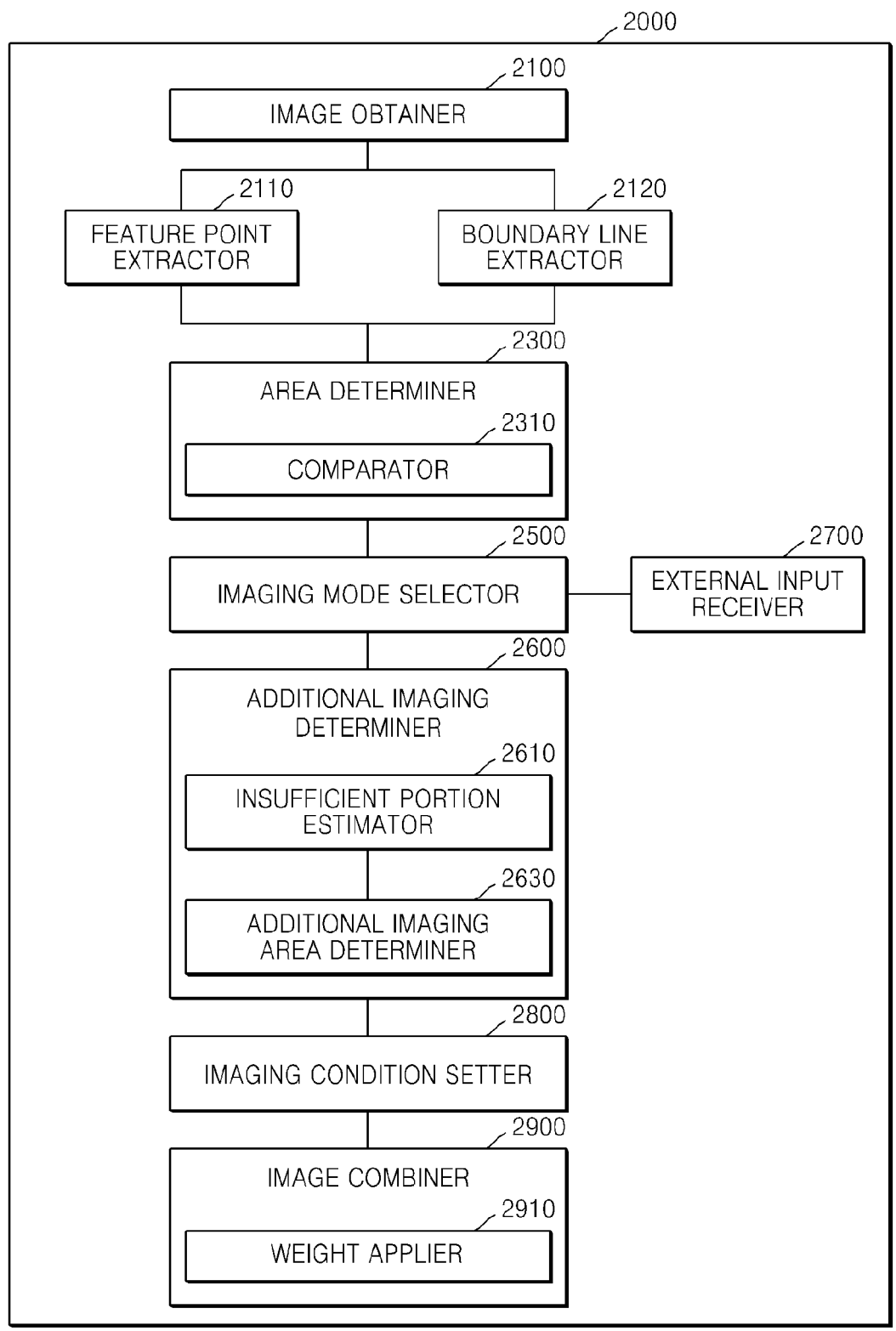
FIG. 30 is a block diagram illustrating an apparatus for obtaining an X-ray image including an ROI of an object, according to an exemplary embodiment.
Figure 31:
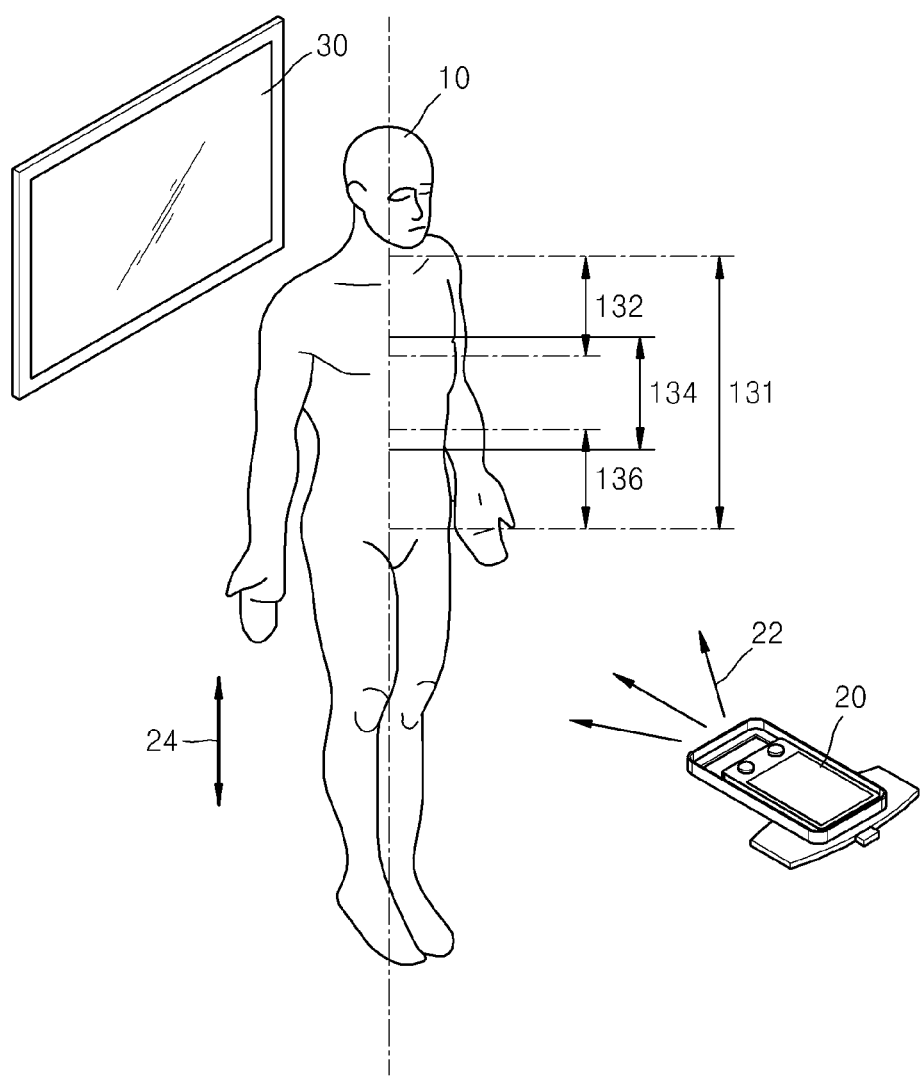
FIG. 31 illustrates an X-ray tube and a detector that are used to obtain an image of an object by sensing an X-ray transmitting through the object.

FIG. 30 is a block diagram illustrating an apparatus 2000 for obtaining an X-ray image including an ROI of an object, according to an exemplary embodiment.

The apparatus 2000 for obtaining an X-ray image including an ROI of an object may include an image obtainer 2100, a feature point extractor 2110, a boundary line extractor 2120, an area determiner 2300, an imaging mode selector 2500, an additional imaging determiner 2600, an external input receiver 2700, an imaging condition setter 2800, and an image combiner 2900.

The area determiner 2300 may further include a comparator 2310. The additional imaging determiner 2600 may further include a sufficient portion estimator 2610 and an additional imaging area determiner 2630. The image combiner 2900 may further include a weight applier 2910.

A method of obtaining an image of an ROI of an object according to an exemplary embodiment may include: obtaining a first image of the object; obtaining a second image of the object; and generating an image including the ROI of the object by using the first image and the second image. The second image may have a different size from the first image and include a portion or the entirety of the ROI. For example, the first image and the second image may have different sizes, and an image including the ROI of the object may be generated by using the first image and the second image. For example, if a kidney and a portion of a ureter are imaged on the first image, the second image including the other portion of the ureter and a bladder is imaged so that all of the kidney, the ureter, and the bladder are included in a combination image generated by using the first image and the second image. According to the above-described exemplary embodiments, the second image may have a different size from the first image and include only a portion of the ROI. Also, according to an exemplary embodiment, the second image including the entire ROI may be obtained.

The second image may be smaller than the first image. In order that an amount of exposure to radiation with respect to the object does not unnecessarily increase, the second image may be smaller than the first image. In the above embodiment, if a kidney and a portion of a ureter are imaged on the first image, the second image including the other portion of the ureter and a bladder is imaged so that an increase in the amount of exposure to radiation with respect to the object is prevented and all of the kidney, the ureter, and the bladder are included in a combination image generated by using the first image and the second image.

For example, when the size of the ROI is the same as or greater than a size of an image that is typically imaged, capturing an image that includes the entire ROI may be dependent upon the skills of the user. Thus, according to an exemplary embodiment, a method of obtaining an image that includes an ROI regardless of the skills of the user may be provided. For example, sizes of a first image and a second image to be imaged may be preset based on a size of an ROI, and the first image and the second image having the determined sizes may be obtained, and an image including the entire ROI may be generated by using the first and second images.

The generating of an image including the ROI of the object by using the first image and the second image according to an exemplary embodiment may include generating an image by combining the first image and the second image by overlapping the first image and the second image by a predetermined size. The first image and the second image may be overlapped by a predetermined size to be generated as a single image. A size of an overlapping portion in the first image and the second image is as described above. In addition, the single image may be referred to as a combination image.

An apparatus for obtaining an image of an ROI of an object according to an exemplary embodiment may include: an image obtainer that obtains a first image and a second image of the object and an image generator that generates an image including the ROI of the object by using the first image and the second image, wherein the second image has a different size from the first image and may include a portion or the entirety of the ROI.

An apparatus for obtaining an image of an ROI of an object according to an exemplary embodiment may include: an image size determiner that determines sizes of a first image and a second image to be imaged based on a size of the ROI; an image obtainer that obtains the first image and the second image of the object based on the determined sizes; and an image generator that generates an image including the ROI of the object by using the first image and the second image, wherein the second image has a different size from the first image and may include a portion or the entirety of the ROI.

The image generator may generate an image by combining the first image and the second image by overlapping the first image and the second image by a predetermined size.

The above-described exemplary methods may be applied to the apparatus according to exemplary embodiments. Thus, a description of the apparatus that is similar to the description of the method will not be repeated here.

In addition, the above-described exemplary embodiments may be applicable to a computer tomography (CT), magnetic resonance imaging (MRI) or other medical imaging systems.

The above-described exemplary embodiments may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs or DVDs).

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. A method of obtaining an image, the method comprising:
    obtaining a first X-ray image of an object with an X-ray source configured to emit an X-ray beam having a first beam width;
    after obtaining the first image, performing, via an image processor, an image analysis of the first image to determine whether the first image includes an entirety of a region of interest (ROI) of the object by comparing the first image and a reference image;
    in response to the performing the image analysis, determining, via the image processor, if a portion of the ROI is absent in the first image with respect to the reference image;
    obtaining a second beam width of the X-ray beam to capture the portion of the ROI absent in the first image when it is determined that the portion of the ROI is absent in the first image;
    configuring the X-ray source to emit the X-ray beam having the second beam width by adjusting at least one among a size and a position of a collimator of the X-ray source, the second beam width made narrower than the first beam width; and
    obtaining a second image of the object to include the portion of the ROI which is absent in the first image with the X-ray source configured to emit the X-ray beam with the second beam width.

2. The method of claim 1, further comprising:
    selecting the reference image from previously stored images based on properties of the object.

3. The method of claim 1, further comprising extracting one or more first feature points of the ROI from the first X-ray image,
    wherein the performing the image analysis of the first image comprises comparing the one or more first feature points with one or more second feature points of a corresponding ROI of the reference image.

4. The method of claim 3, wherein a number and positions of the one or more first feature points are defined in advance, based on different criteria including at least one among a size of the ROI and a position of the ROI within the object.

5. The method of claim 3, wherein the comparing the one or more first feature points with the one or more second feature points comprises:
    comparing a number and positions of the one or more second feature points and a number and positions of the one or more first feature points,
    wherein the first image is determined to include the ROI when the number of the one or more second feature points coincide with that of the one or more first feature points and the positions of the one or more second feature points substantially coincide with that of the one or more first feature points.

6. The method of claim 1, further comprising extracting a first boundary line of the ROI from the first image,
    wherein the performing the image analysis of the first image comprises comparing the first boundary line and a second boundary line of a corresponding ROI of the reference image.

7. The method of claim 6, wherein the comparing the first boundary line and the second boundary line comprises determining a similarity between the first boundary line and the second boundary line,
    wherein the first image is determined to include the ROI when the first boundary line is substantially similar to the second boundary line.

8. The method of claim 1, wherein the obtaining the second image comprises providing a first imaging mode and a second imaging mode to be selected to re-image the object based on the image analysis, the first imaging mode is a mode in which an entire ROI of the object is re-imaged, and the second imaging mode is a mode in which the portion of the ROI of the object is re-imaged.

9. The method of claim 8, further comprising:

receiving a determination of the portion of the ROI to be re-imaged;

selecting the second imaging mode; and obtaining the second image including the determined portion of the ROI, in the second imaging mode.

10. The method of claim 9, wherein the receiving the determination of the portion of the ROI to be re-imaged comprises:

estimating the portion of the ROI that is not included in the first image; and receiving a determination of an additional imaging area to include the estimated portion by using size information of the first image.

11. The method of claim 10, wherein the estimating the portion of the ROI comprises:

determining a size and a position of the portion not included in the first image based on the size and the position of the ROI included in the reference image.

12. The method of claim 8, further comprising:

receiving a selection of an additional imaging area of the object;

selecting the second imaging mode; and obtaining the second image corresponding to the received additional imaging area, in the second imaging mode.

13. The method of claim 8, further comprising:

selecting the first imaging mode or the second imaging mode based on the received determination;

setting an imaging condition based on the selected first imaging mode or the second imaging mode, wherein the obtaining the second image comprises obtaining an X-ray image of the object according to the set imaging condition.

14. The method of claim 9, further comprising combining the first image and the second image.

15. An apparatus for obtaining an image of a region of interest (ROI) of an object, the apparatus comprising:

a processor configured to obtain a first image of an object with an X-ray source configured to emit an X-ray beam having a first beam width; perform an image analysis of the first image; determine, in response to the performing the image analysis after obtaining the first image, whether the first image includes an entirety of a region of interest (ROI) of the object, by comparing the first image and a reference image; and set a second beam width of the X-ray beam to capture a portion of the ROI absent in the first image, when it is determined that the portion of the ROI is absent in the first image with respect to the reference image, the second beam width made narrower than the first beam width, wherein the X-ray source is configured to emit the X-ray beam having the second beam width by adjusting at least one among a size and a position of a collimator of the X-ray source, the processor is configured to obtain a second image of the object to include the portion of the ROI which is absent in the first image, in response to a determination that the portion of the ROI is absent in the first image, and the obtained second image includes the portion of the ROI which has not been imaged in the first image.

16. The apparatus of claim 15, wherein the reference image is selected based on properties of the object from previously stored images.

17. The apparatus of claim 15, wherein the processor is configured to perform the image analysis by extracting one or more first feature points related to the ROI from the first image, and comparing the one or more first feature points with one or more second feature points of a corresponding ROI of the reference image.

18. An imaging method comprising:

obtaining a main image in a main imaging operation set to image a region of interest (ROI) of an object with an X-ray source configured to emit an X-ray beam having a first beam width;

after obtaining the main image, performing, via an image processor, an image analysis of the main image to determine whether the main image includes an entirety of a region of interest (ROI) of the object, by comparing the main image and a reference image;

in response to the performing the image analysis, determining, via the image processor, if a portion of the ROI is absent in the main image with respect to the reference image;

obtaining a second beam width of the X-ray beam to capture the portion of the ROI absent in the main image when it is determined that the portion of the ROI is absent in the main image;

configuring the X-ray source to emit the X-ray beam having the second beam width by adjusting at least one among a size and a position of a collimator of the X-ray source, the second beam width made narrower than the first beam width; and obtaining an additional image of the object to include the portion of the ROI absent in the main image with the X-ray source configured to emit the X-ray beam with the second beam width, in an auxiliary imaging operation.

19. An apparatus for obtaining an image of a region of interest (ROI) of an object, the apparatus comprising:

a processor configured to determine sizes of a first image and a second image to be imaged based on a size of the ROI; obtain the first image and the second image of the object based on the determined sizes with an X-ray source configured to emit an X-ray beam having a first beam width; generate a combined image by using the first image and the second image; determine, after obtaining the combined image, whether the combined image includes an entirety of a region of interest (ROI) of the object by comparing the combined image and a reference image; and set a second beam width of the X-ray beam to capture a portion of the ROI absent in the combined image, when it is determined that the portion of the ROI is absent in the combined image with respect to the reference image, the second beam width made narrower than the first beam width, wherein the X-ray source is configured to emit the X-ray beam having the second beam width by adjusting at least one among a size and a position of a collimator of the X-ray source, the processor is configured to re-obtain a portion of the second image to include the portion of the ROI which is absent in the combined image, in response to a determination that the portion of the ROI is absent in the combined image, and the re-obtained portion of the second image has a size smaller than that of the first image or the second image.

* * * * *